United States Patent
Hu et al.

(10) Patent No.: US 10,946,092 B1
(45) Date of Patent: Mar. 16, 2021

(54) ANTIBODIES BINDING LAG3 AND METHODS OF TREATMENT USING THEM

(71) Applicants: Beijing Mabworks Biotech Co., Ltd., Beijing (CN); Beijing Mabridge Biopharmaceutical Co., Ltd., Beijing (CN)

(72) Inventors: Wenqi Hu, Beijing (CN); Jiangmei Li, Beijing (CN); Feng Li, Beijing (CN)

(73) Assignees: BEIJING MABWORKS BIOTECH CO., LTD., Beijing (CN); BEIJING MABRIDGE BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 16/983,188

(22) Filed: Aug. 3, 2020

(30) Foreign Application Priority Data

Jun. 5, 2020 (CN) .......... 202010509498.X

(51) Int. Cl.
| *A61K 39/395* | (2006.01) |
| *A61K 38/20* | (2006.01) |
| *A61P 35/00* | (2006.01) |
| *C07K 16/28* | (2006.01) |
| *A61K 39/00* | (2006.01) |
| *A61K 45/06* | (2006.01) |

(52) U.S. Cl.
CPC ........ *A61K 39/39541* (2013.01); *A61K 38/20* (2013.01); *A61K 38/2013* (2013.01); *A61K 39/3955* (2013.01); *A61K 39/39558* (2013.01); *A61K 45/06* (2013.01); *A61P 35/00* (2018.01); *C07K 16/2803* (2013.01); *A61K 2039/505* (2013.01); *A61K 2039/507* (2013.01); *C07K 2317/21* (2013.01); *C07K 2317/24* (2013.01); *C07K 2317/565* (2013.01); *C07K 2317/74* (2013.01); *C07K 2317/92* (2013.01)

(58) Field of Classification Search
None
See application file for complete search history.

(56) References Cited

U.S. PATENT DOCUMENTS

| 9,005,629 | B2 * | 4/2015 | Pardoll | A61P 11/06 424/184.1 |
| 9,902,772 | B2 * | 2/2018 | Zhou | A61P 35/00 |
| 9,908,936 | B2 * | 3/2018 | Triebel | A61P 37/02 |
| 10,188,730 | B2 * | 1/2019 | Liang | A61P 37/02 |
| 10,344,089 | B2 * | 7/2019 | Thudium | A61P 35/02 |
| 10,577,421 | B2 * | 3/2020 | Fang | C07K 16/2803 |
| 2017/0198037 | A1 * | 7/2017 | Bonvini | A61P 31/00 |
| 2017/0334995 | A1 * | 11/2017 | Zettl | C07K 16/2818 |
| 2019/0135916 | A1 * | 5/2019 | Haudebourg | A61P 7/06 |
| 2020/0172617 | A1 * | 6/2020 | Stein | A61K 39/0011 |

* cited by examiner

*Primary Examiner* — Elly-Gerald Stoica
(74) *Attorney, Agent, or Firm* — Duane Morris LLP; Thomas J. Kowalski; Deborah L. Lu

(57) ABSTRACT

An isolated monoclonal antibody or an antigen-binding portion thereof that specifically binds human LAG3. A nucleic acid molecule encoding the antibody or antigen-binding portion thereof, an expression vector, a host cell and a method for expressing the antibody or antigen-binding portion thereof are also provided. The present disclosure further provides an immuneconjugate, a bispecific molecule, a chimeric antigen receptor, and a pharmaceutical composition comprising the antibody or antigen-binding portion thereof thereof, as well as a treatment method using the same.

20 Claims, 10 Drawing Sheets
Specification includes a Sequence Listing.

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: VH-CDR1 of mouse, chimeric and humanized (with
      or without affinity maturation) 101F4 antibodies

<400> SEQUENCE: 1

Asp Tyr Glu Met His
1               5

<210> SEQ ID NO 2
<211> LENGTH: 17
<212> TYPE: PRT
<213> ORGANISM: Artificial Sequence
<220> FEATURE:
<223> OTHER INFORMATION: VH-CDR2 of mouse, chimeric and humanized (with
      or without affinity maturation) 101F4 antibodies

```
<400> SEQUENCE: 2

Ala Ile Asp Pro Glu Thr Gly Gly Ile Val Tyr Asn Gln Arg Phe Lys
1               5                   10                  15
Gly

<210> SEQ ID NO 3
<211> LENGTH: 5
<212> TYPE: PRT
<213> ORGANISM: Artificial Sequence
<220> FEATURE:
<223> OTHER INFORMATION: VH-CDR3 of mouse, chimeric and humanized
      (without affinity maturation) 101F4 antibodies

<400> SEQUENCE: 3

Ala Gly Trp Gly Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: VH-CDR3 of humanized (with affinity maturation)
      101F4 antibodies

<400> SEQUENCE: 4

Thr Gly Trp Asn Asp
1               5

<210> SEQ ID NO 5
<211> LENGTH: 11
<212> TYPE: PRT
<213> ORGANISM: Artificial Sequence
<220> FEATURE:
<223> OTHER INFORMATION: VL-CDR1 of mouse, chimeric and humanized (with
      or without affinity maturation) 101F4 antibodies

<400> SEQUENCE: 5

Lys Ala Ser Gln Asp Ile Asn Ser Tyr Leu Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: VL-CDR2 of mouse, chimeric and humanized (with
      or without affinity maturation) 101F4 antibodies

<400> SEQUENCE: 6

Arg Ala Asn Arg Leu Leu Asp
1               5

<210> SEQ ID NO 7
<211> LENGTH: 9
<212> TYPE: PRT
<213> ORGANISM: Artificial Sequence
<220> FEATURE:
<223> OTHER INFORMATION: VL-CDR3 of mouse, chimeric and humanized
      (without affinity maturation) 101F4 antibodies

<400> SEQUENCE: 7

Leu Gln Tyr Asp Glu Phe Pro Phe Thr
1               5

<210> SEQ ID NO 8
```

```
<211> LENGTH: 9
<212> TYPE: PRT
<213> ORGANISM: Artificial Sequence
<220> FEATURE:
<223> OTHER INFORMATION: VL-CDR3 of humanized (with affinity maturation)
      101F4 antibodies

<400> SEQUENCE: 8

Gln Gln Tyr Asp Glu Phe Pro Phe Thr
1               5

<210> SEQ ID NO 9
<211> LENGTH: 114
<212> TYPE: PRT
<213> ORGANISM: Artificial Sequence
<220> FEATURE:
<223> OTHER INFORMATION: VH of mouse and chimeric 101F4 antibodies

<400> SEQUENCE: 9

Glu Val Gln Leu Glu Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val Tyr Gly Leu Glu Trp Met
            35                  40                  45

Gly Ala Ile Asp Pro Glu Thr Gly Gly Ile Val Tyr Asn Gln Arg Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Ala Gly Trp Gly Tyr Trp Gly Gln Gly Thr Thr Leu Thr Val
            100                 105                 110

Ser Ser

<210> SEQ ID NO 10
<211> LENGTH: 114
<212> TYPE: PRT
<213> ORGANISM: Artificial Sequence
<220> FEATURE:
<223> OTHER INFORMATION: VH of humanized antibody 101F4H0L0

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Ala Ile Asp Pro Glu Thr Gly Gly Ile Val Tyr Asn Gln Arg Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gly Trp Gly Tyr Trp Gly Gln Gly Thr Thr Val Thr Val
            100                 105                 110

Ser Ser
```

-continued

```
<210> SEQ ID NO 11
<211> LENGTH: 114
<212> TYPE: PRT
<213> ORGANISM: Artificial Sequence
<220> FEATURE:
<223> OTHER INFORMATION: VH of humanized antibodies 101F4H2L2 and
      101F4H2L3

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Ala Ile Asp Pro Glu Thr Gly Gly Ile Val Tyr Asn Gln Arg Phe
        50                  55                  60

Lys Gly Arg Val Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gly Trp Gly Tyr Trp Gly Gln Gly Thr Thr Val Thr Val
            100                 105                 110

Ser Ser

<210> SEQ ID NO 12
<211> LENGTH: 114
<212> TYPE: PRT
<213> ORGANISM: Artificial Sequence
<220> FEATURE:
<223> OTHER INFORMATION: VH of humanized antibodies 101F4H3L2 and
      101F4H3L3

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Ala Ile Asp Pro Glu Thr Gly Gly Ile Val Tyr Asn Gln Arg Phe
        50                  55                  60

Lys Gly Arg Ala Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Gly Ala Gly Trp Gly Tyr Trp Gly Gln Gly Thr Thr Val Thr Val
            100                 105                 110

Ser Ser

<210> SEQ ID NO 13
<211> LENGTH: 114
<212> TYPE: PRT
<213> ORGANISM: Artificial Sequence
<220> FEATURE:
<223> OTHER INFORMATION: VH of humanized (with affinity maturation)
      antibodies 101F4H2L2-8 and 101F4H2L3-8

<400> SEQUENCE: 13

Gln Val Gln Leu Val Gln Ser Gly Ala Glu Val Lys Lys Pro Gly Ala
```

```
                1               5                  10                  15
Ser Val Lys Val Ser Cys Lys Val Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Ala Ile Asp Pro Glu Thr Gly Gly Ile Val Tyr Asn Gln Arg Phe
        50                  55                  60

Lys Gly Arg Val Thr Leu Thr Ala Asp Thr Ser Thr Asp Thr Ala Tyr
 65                 70                  75                  80

Met Glu Leu Ser Ser Leu Arg Ser Glu Asp Thr Ala Val Tyr Tyr Cys
                85                  90                  95

Ala Thr Thr Gly Trp Asn Asp Trp Gly Gln Gly Thr Thr Val Thr Val
                100                 105                 110

Ser Ser

<210> SEQ ID NO 14
<211> LENGTH: 114
<212> TYPE: PRT
<213> ORGANISM: Artificial Sequence
<220> FEATURE:
<223> OTHER INFORMATION: VH of humanized (with affinity maturation)
      antibody 101F4H3L3-8

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Lys Gly Leu Glu Trp Met
            35                  40                  45

Gly Ala Ile Asp Pro Glu Thr Gly Gly Ile Val Tyr Asn Gln Arg Phe
        50                  55                  60

Lys Gly Arg Ala Thr Leu Thr Ala Asp Thr Ser Thr Asp Thr Ala Tyr
 65                 70                  75                  80

Met Glu Leu Ser Ser Leu Arg Ser Glu Asp Thr Ala Val Tyr Tyr Cys
                85                  90                  95

Ala Gly Thr Gly Trp Asn Asp Trp Gly Gln Gly Thr Thr Val Thr Val
                100                 105                 110

Ser Ser

<210> SEQ ID NO 15
<211> LENGTH: 107
<212> TYPE: PRT
<213> ORGANISM: Artificial Sequence
<220> FEATURE:
<223> OTHER INFORMATION: VL of mouse and chimeric 101F4 antibodies

<400> SEQUENCE: 15

Asp Ile Val Ile Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Leu Asp Gly Val Pro Ser Arg Phe Ser Gly
        50                  55                  60

Ser Gly Ser Gly Gln Asp Tyr Ser Leu Thr Ile Ser Ser Leu Glu Phe
```

```
                65                  70                  75                  80
Glu Asp Met Gly Leu Tyr Tyr Cys Leu Gln Tyr Asp Glu Phe Pro Phe
                        85                  90                  95

Thr Phe Gly Ser Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: VL of humanized antibody 101F4H0L0

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: VL of humanized antibodies 101F4H2L2 and
      101F4H3L2

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: VL of humanized (with affinity maturation)
      antibody 101F4H2L2-8
```

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Gln Gln Tyr Asp Glu Phe Pro Phe
                85                  90                  95

Thr Phe Gly Gln Gly Thr Lys Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: VL of humanized antibodies 101F4H2L3 and
      101F4H3L3

<400> SEQUENCE: 19

Asp Ile Gln Ile Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: VL of humanized (with affinity maturation)
      antibodies 101F4H2L3-8 and 101F4H3L3-8

<400> SEQUENCE: 20

Asp Ile Gln Ile Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Leu Asp Gly Val Pro Ser Arg Phe Ser Gly
    50                  55                  60

```
Ser Gly Ser Gly Gln Asp Tyr Thr Leu Thr Ile Ser Ser Leu Gln Pro
 65                  70                  75                  80

Glu Asp Phe Ala Thr Tyr Tyr Cys Gln Gln Tyr Asp Glu Phe Pro Phe
                 85                  90                  95

Thr Phe Gly Gln Gly Thr Lys Leu Glu Ile Lys
            100                 105

<210> SEQ ID NO 21
<211> LENGTH: 5
<212> TYPE: PRT
<213> ORGANISM: Artificial Sequence
<220> FEATURE:
<223> OTHER INFORMATION: VH-CDR1 of mouse, chimeric and humanized 134G10
      antibodies

<400> SEQUENCE: 21

Ser Phe Gly Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: VH-CDR2 of mouse, chimeric and humanized 134G10
      antibodies

<400> SEQUENCE: 22

Ile Ile Ser Ser Gly Gly Thr Tyr Thr Phe Tyr Pro Asp Ile Leu Lys
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: VH-CDR3 of mouse, chimeric and humanized 134G10
      antibodies

<400> SEQUENCE: 23

Val Tyr Ser Asp Tyr Asp Gly Arg Phe Asp Tyr
1               5                   10

<210> SEQ ID NO 24
<211> LENGTH: 17
<212> TYPE: PRT
<213> ORGANISM: Artificial Sequence
<220> FEATURE:
<223> OTHER INFORMATION: VL-CDR1 of mouse, chimeric and humanized 134G10
      antibodies

<400> SEQUENCE: 24

Lys Ser Ser Gln Ser Leu Leu Asn Ser Gly Asn Gln Lys Asn Tyr Leu
1               5                   10                  15

Ala

<210> SEQ ID NO 25
<211> LENGTH: 7
<212> TYPE: PRT
<213> ORGANISM: Artificial Sequence
<220> FEATURE:
<223> OTHER INFORMATION: VL-CDR2 of mouse, chimeric and humanized 134G10
      antibodies

<400> SEQUENCE: 25
```

-continued

Gly Ala Ser Thr Arg Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: VL-CDR3 of mouse, chimeric and humanized 134G10
      antibodies

<400> SEQUENCE: 26

Gln Asn Asp His Ser Tyr Pro Leu Thr
1               5

<210> SEQ ID NO 27
<211> LENGTH: 120
<212> TYPE: PRT
<213> ORGANISM: Artificial Sequence
<220> FEATURE:
<223> OTHER INFORMATION: VH of mouse and chimeric 134G10 antibodies

<400> SEQUENCE: 27

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
            20                  25                  30

Gly Met Ser Trp Val Arg Gln Thr Pro Asp Lys Arg Leu Glu Trp Val
        35                  40                  45

Gly Ile Ile Ser Ser Gly Gly Thr Tyr Thr Phe Tyr Pro Asp Ile Leu
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Val Tyr Ser Asp Tyr Asp Gly Arg Phe Asp Tyr Trp Gly Gln
            100                 105                 110

Gly Thr Leu Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: VH of humanized antibody 134G10H0L0

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ile Ile Ser Ser Gly Gly Thr Tyr Thr Phe Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Asp Tyr Asp Gly Arg Phe Asp Tyr Trp Gly Gln
            100                 105                 110

Gly Thr Leu Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: VH of humanized antibodies 134G10H2L2 and
      134G10H2L3

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Arg Leu Glu Trp Val
        35                  40                  45

Ser Ile Ile Ser Ser Gly Gly Thr Tyr Thr Phe Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Asp Tyr Asp Gly Arg Phe Asp Tyr Trp Gly Gln
            100                 105                 110

Gly Thr Leu Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: VH of humanized antibodies 134G10H3L2 and
      134G10H3L3

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Arg Leu Glu Trp Val
        35                  40                  45

Gly Ile Ile Ser Ser Gly Gly Thr Tyr Thr Phe Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Asp Tyr Asp Gly Arg Phe Asp Tyr Trp Gly Gln
            100                 105                 110

Gly Thr Leu Val Thr Val Ser Ser
        115                 120

<210> SEQ ID NO 31

```
<211> LENGTH: 113
<212> TYPE: PRT
<213> ORGANISM: Artificial Sequence
<220> FEATURE:
<223> OTHER INFORMATION: VL of mouse and chimeric antibodies 134G10

<400> SEQUENCE: 31

Asp Ile Val Met Thr Gln Ser Pro Ser Ser Leu Ser Val Ser Ala Gly
1               5                  10                  15

Glu Lys Val Thr Met Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys

<210> SEQ ID NO 32
<211> LENGTH: 113
<212> TYPE: PRT
<213> ORGANISM: Artificial Sequence
<220> FEATURE:
<223> OTHER INFORMATION: VL of humanized antibody 134G10H0L0

<400> SEQUENCE: 32

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Gln Gly Thr Lys Leu Glu Ile
            100                 105                 110

Lys

<210> SEQ ID NO 33
<211> LENGTH: 113
<212> TYPE: PRT
<213> ORGANISM: Artificial Sequence
<220> FEATURE:
<223> OTHER INFORMATION: VL of humanized antibodies 134G10H2L2 and
      134G10H3L2

<400> SEQUENCE: 33

Asp Ile Val Met Thr Gln Ser Pro Ser Ser Leu Ala Val Ser Leu Gly
1               5                  10                  15

Glu Arg Ala Thr Ile Asn Cys Lys Ser Ser Gln Ser Leu Leu Asn Ser
```

```
                20                  25                  30
Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Ala Gly Thr Lys Leu Glu Ile
              100                 105                 110

Lys
```

<210> SEQ ID NO 34
<211> LENGTH: 113
<212> TYPE: PRT
<213> ORGANISM: Artificial Sequence
<220> FEATURE:
<223> OTHER INFORMATION: VL of humanized antibodies 134G10H2L3 and
      134G10H3L3

<400> SEQUENCE: 34

```
Asp Ile Val Met Thr Gln Ser Pro Ser Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Ala Gly Thr Lys Leu Glu Ile
              100                 105                 110

Lys
```

<210> SEQ ID NO 35
<211> LENGTH: 327
<212> TYPE: PRT
<213> ORGANISM: Artificial Sequence
<220> FEATURE:
<223> OTHER INFORMATION: human IgG4 heavy chain constant region with
      S228P mutation

<400> SEQUENCE: 35

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
 65                 70                  75                  80
```

```
Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 36
<211> LENGTH: 107
<212> TYPE: PRT
<213> ORGANISM: Artificial Sequence
<220> FEATURE:
<223> OTHER INFORMATION: human kappa light chain constant region

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 37
<211> LENGTH: 1578
<212> TYPE: DNA
<213> ORGANISM: Homo sapiens

<400> SEQUENCE: 37

| | | | | | | |
|---|---|---|---|---|---|---|
| atgtgggagg | cccagttcct | gggcctgctg | ttcctgcagc | ccctgtgggt | ggccccgtg | 60 |
| aagcccctgc | agcccggcgc | cgaggtgccc | gtggtgtggg | cccaggaggg | cgcccccgcc | 120 |
| cagctgccct | gcagccccac | catcccctg | caggacctga | gcctgctgcg | ccgcgccggc | 180 |
| gtgacctggc | agcaccagcc | cgacagcggc | cccccgccg | ccgcccccgg | ccacccctg | 240 |
| gcccccggcc | cccaccccgc | cgcccccagc | agctggggcc | ccgcccccg | ccgctacacc | 300 |
| gtgctgagcg | tgggcccgg | cggcctgcgc | agcggccgcc | tgcccctgca | gcccgcgtg | 360 |
| cagctggacg | agcgcggccg | ccagcgcggc | gacttcagcc | tgtggctgcg | ccccgcccgc | 420 |
| cgcgccgacg | ccggcgagta | ccgcgccgcc | gtgcacctgc | gcgaccgcgc | cctgagctgc | 480 |
| cgcctgcgcc | tgcgcctggg | ccaggccagc | atgaccgcca | gccccccgg | cagcctgcgc | 540 |
| gccagcgact | gggtgatcct | gaactgcagc | ttcagccgcc | ccgaccgccc | cgccagcgtg | 600 |
| cactggttcc | gcaaccgcgg | ccagggccgc | gtgcccgtgc | gcgagagccc | ccaccaccac | 660 |
| ctggccgaga | gcttcctgtt | cctgccccag | gtgagcccca | tggacagcgg | cccctggggc | 720 |
| tgcatcctga | cctaccgcga | cggcttcaac | gtgagcatca | tgtacaacct | gaccgtgctg | 780 |
| ggcctggagc | ccccacccc | cctgaccgtg | tacgccggcg | ccggcagccg | cgtgggcctg | 840 |
| ccctgccgcc | tgcccgccgg | cgtgggcacc | cgcagcttcc | tgaccgccaa | gtggacccc | 900 |
| cccggcggcg | ccccgacct | gctggtgacc | ggcgacaacg | gcgacttcac | cctgcgcctg | 960 |
| gaggacgtga | gccaggccca | ggccggcacc | tacacctgcc | acatccacct | gcaggagcag | 1020 |
| cagctgaacg | ccaccgtgac | cctggccatc | atcaccgtga | ccccaagag | cttcggcagc | 1080 |
| cccggcagcc | tgggcaagct | gctgtgcgag | gtgaccccg | tgagcggcca | ggagcgcttc | 1140 |
| gtgtggagca | gcctggacac | cccagccag | cgcagcttca | gcggcccctg | gctggaggcc | 1200 |
| caggaggccc | agctgctgag | ccagccctgg | cagtgccagc | tgtaccaggg | cgagcgcctg | 1260 |
| ctgggcgccg | ccgtgtactt | caccgagctg | agcagccccg | gcgcccagcg | cagcggccgc | 1320 |
| gcccccggcg | ccctgcccgc | cggccacctg | ctgctgttcc | tgatcctggg | cgtgctgagc | 1380 |
| ctgctgctgc | tggtgaccgg | cgccttcggc | ttccacctgt | ggcgccgcca | gtggcgcccc | 1440 |
| cgccgcttca | cgccctgga | gcagggcatc | acccccccc | aggcccagag | caagatcgag | 1500 |
| gagctggagc | aggagcccga | gcccgagccc | gagcccgagc | ccgagcccga | gcccgagccc | 1560 |
| gagcccgagc | agctgtaa | | | | | 1578 |

<210> SEQ ID NO 38
<211> LENGTH: 1602
<212> TYPE: DNA
<213> ORGANISM: Macaca mulatta

<400> SEQUENCE: 38

| | | | | | | |
|---|---|---|---|---|---|---|
| atgtgggagg | cccagttcct | gggcctgctg | ttcctgcagc | ccctgtgggt | ggccccgtg | 60 |
| aagccccccc | agcccggcgc | cgagatcagc | gtggtgtggg | cccaggaggg | cgcccccgcc | 120 |
| cagctgccct | gcagccccac | catcccctg | caggacctga | gcctgctgcg | ccgcgccggc | 180 |
| gtgacctggc | agcaccagcc | cgacagcggc | cccccgccc | cgcccccgg | ccaccccccc | 240 |
| gcccccggcc | accgcccgc | cgcccccctac | agctggggcc | ccgcccccg | ccgctacacc | 300 |

```
gtgctgagcg tgggccccgg cggcctgcgc agcggccgcc tgcccctgca gccccgcgtg      360
cagctggacg agcgcggccg ccagcgcggc gacttcagcc tgtggctgcg ccccgcccgc      420
cgcgccgacg ccggcgagta ccgcgccacc gtgcacctgc gcgaccgcgc cctgagctgc      480
cgcctgcgcc tgcgcgtggg ccaggccagc atgaccgcca gccccccggg cagcctgcgc      540
accagcgact gggtgatcct gaactgcagc ttcagccgcc ccgaccgccc cgccagcgtg      600
cactggttcc gcagccgcgg ccagggccgc gtgcccgtgc agggcagccc caccaccac       660 ctggccgaga gcttcctgtt cctgccccac gtgggcccca tggacagcgg cctgtggggc      720
tgcatcctga cctaccgcga cggcttcaac gtgagcatca tgtacaacct gaccgtgctg      780
ggcctggagc ccgccacccc cctgaccgtg tacgccggcg ccggcagccg cgtggagctg      840
ccctgccgcc tgccccccgc cgtgggcacc cagagcttcc tgaccgccaa gtgggccccc      900
cccggcggcg ccccgacct gctggtggcc ggcgacaacg cgacttcac cctgcgcctg        960 gaggacgtga ccaggccca ggccggcacc tacatctgcc acatccgcct gcagggccag      1020
cagctgaacg ccaccgtgac cctggccatc atcaccgtga ccccaagag cttcggcagc      1080 cccggcagct gggcaagct gctgtgcgag gtgaccccg ccagcggcca ggagcacttc       1140
gtgtggagcc ccctgaacac ccccagccag cgcagcttca gcggcccctg ctggaggcc      1200 caggaggccc agctgctgag ccagccctgg cagtgccagc tgcaccaggg cgagaccctg     1260
ctgggcgccg ccgtgtactt caccgagctg agcagccccg cgcccagcg cagcggccgc      1320 gccccggcg ccctgcgcgc cggccacctg ccctgttcc tgatcctggg cgtgctgttc       1380
ctgctgctgc tggtgaccgg cgccttcggc ttccacctgt ggcgccgcca gtggcgcccc     1440
cgccgcttca gcgccctgga gcagggcatc caccccccc aggcccagag caagatcgag      1500
gagctggagc aggagcccga gctggagccc gagcccgagc tggagcgcga gctgggcccc     1560
gagcccgagc ccggccccga gcccgagccc gagcagctgt aa                       1602

<210> SEQ ID NO 39
<211> LENGTH: 1566
<212> TYPE: DNA
<213> ORGANISM: Mus musculus

<400> SEQUENCE: 39
atgcgcgagg acctgctgct gggcttcctg ctgctgggcc tgctgtggga ggccccgtg        60 gtgagcagcg cccccggcaa ggagctgccc gtggtgtggg cccaggaggg cgccccgtg       120 cacctgccct gcagctgaa gagccccaac ctggacccca cttcctgcg ccgcggcggc       180 gtgatctggc agcaccagcc cgacagcggc cagcccaccc ccatcccgc cctggacctg      240 caccagggca tgcccagccc ccgccagccc gccccggcc gctacaccgt gctgagcgtg       300 gccccggcg gcctgcgcag cggccgccag ccctgcacc ccacgtgca gctggaggag        360 cgcggcctgc agcgcggcga cttcagcctg tggctgcgcc ccgccctgcg caccgacgcc      420
ggcgagtacc acgccaccgt gcgcctgccc aaccgcgccc tgagctgcag cctgcgcctg      480
cgcgtgggcc aggccagcat gatcgccagc cccagcggcg tgctgaagct gagcgactgg      540
gtgctgctga actgcagctt cagccgcccc gaccgccccg tgagcgtgca ctggttccag      600
ggccagaacc gcgtgcccgt gtacaacagc cccgccact tcctggccga gaccttcctg      660
ctgctgcccc aggtgagccc cctggacagc ggcacctggg gctgcgtgct gacctaccgc     720
gacggcttca cgtgagcat cacctacaac ctgaaggtgc tgggcctgga gcccgtggcc      780
```

```
cccctgaccg tgtacgccgc cgagggcagc cgcgtggagc tgccctgcca cctgccccc     840 ggcgtgggca cccccagcct gctgatcgcc aagtggaccc ccccggcgg cggccccgag     900 ctgcccgtgg ccggcaagag cggcaacttc accctgcacc tggaggccgt gggcctggcc    960
caggccggca cctacacctg cagcatccac ctgcagggcc agcagctgaa cgccaccgtg   1020
accctggccg tgatcaccgt gacccccaag agcttcggcc tgcccggcag ccgcggcaag   1080
ctgctgtgcg aggtgacccc cgccagcggc aaggagcgct tcgtgtggcg ccccctgaac   1140
aacctgagcc gcagctgccc cggccccgtg ctggagatcc aggaggcccg cctgctggcc   1200
gagcgctggc agtgccagct gtacgagggc cagcgcctgc tgggcgccac cgtgtacgcc   1260
gccgagagca gcagcggcgc ccacagcgcc cgccgcatca gcggcgacct gaagggcggc   1320
cacctggtgc tggtgctgat cctgggcgcc ctgagcctgt tcctgctggt ggccggcgcc   1380
ttcggcttcc actggtggcg caagcagctg ctgctgcgcc gcttcagcgc cctggagcac   1440
ggcatccagc ccttccccgc ccagcgcaag atcgaggagc tggagcgcga gctggagacc   1500
gagatgggcc aggagcccga gcccgagccc gagcccagc tggagcccga gccccgccag   1560
ctgtaa                                                              1566
```

ANTIBODIES BINDING LAG3 AND METHODS OF TREATMENT USING THEM

RELATED APPLICATIONS AND INCORPORATION BY REFERENCE

This application claims priority to Chinese Patent Application No. 202010509498.X filed on Jun. 5, 2020.

The foregoing application, and all documents cited therein or during its prosecution ("appin cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

Citation or identification of any document in this application is not an admission that such document is available as prior art to the present disclosure.

FIELD OF THE INVENTION

The disclosure relates to an antibody or an antigen binding portion thereof specifically binding to human LAG3, preparation and use thereof, especially its use in treatment of human diseases associated with LAG3, such as cancers, infectious diseases, and inflammatory diseases such as autoimmune diseases.

BACKGROUND OF THE INVENTION

Immune response is a complex process during which stimulatory or inhibitory molecules on immune cells are activated or inactivated to keep the response at an appropriate or optimal level. For example, the inhibitory receptors such as PD-1 and CTLA-4 are sometimes up-regulated to balance the co-stimulatory receptor activity and limit immune cell activation, thus preventing autoimmunity or auto-inflammation. However, such suppressive mechanism may be manipulated by tumor cells to protect them from immune attack, leading to cancer initiation and progression. During pathogen infection, especially chronic infection, lymphocyte activation gene 3 (LAG3) is also expressed at a high level, leading to immunosuppression and development of diseases, including sepsis, leprosy, and acquired immunodeficiency syndrome (AIDS) (Bunn P A, Jr. (1998) *Seminars in Oncology*, 25 (2 suppl 6):1-3). Antibodies targeting PD-1 and CTLA-4 have been approved for clinic cancer treatment, but a lot of cancer patients are not responsive (Topalian S L et al., (2012) *The New England journal of medicine* 366: 2443-2454). Therefore, attention has been turned to additional inhibitory receptors such as LAG3 and T cell immunoglobulin and mucindomain containing-3 (TIM3) (Anderson A C et al., (2016) *Immunity* 44: 989-1004).

LAG3, also known as CD223, is a type I transmembrane protein structurally similar to CD4. It was firstly found on activated T and NK cells and suggested to play a negative regulatory role in controlling T cell activation and function and NK cell proliferation (Turnis M E et al., (2015) *European journal of immunology* 45: 1892-1905). In specific, dimerized LAG3 molecules on the cell surface may stably bind MHC class II molecules, and the LAG3-MHC II interaction attenuates the immune response via down-regulation of antigen-dependent CD4+ and CD8+ T cell stimulation. For example, the binding of MHC class II molecules on melanoma cells to LAG3 on infiltrating T cells may facilitate T cell exhaustion, which is not evident in MHC II-negative tumor cell lines (Hemon P et al., (2011) *Journal of immunology* 186: 5173-5183). Excessive LAG3 molecules may be degraded in lysosomal compartments or cleaved from the T cell surface by metalloproteinases ADAM10 and ADAM17 to attenuate the immune-suppression (Clayton K L et al., (2015) *Journal of virology* 89: 3723-3736; Bae J et al., (2014) *Journal of immunology* 193: 3101-3112; Woo S R et al., (2010) *European journal of immunology* 40: 1768-1777).

LAG3 may also bind Galectin-3 or LSECtin, leading to CD8+ T cell suppression within the tumor microenvironment and IFNγ production inhibition by antigen-specific effector T cells, respectively (Kouo T et al., (2015) *Cancer Immunol Res.* 3: 412-423; Xu F et al., (2014) *Cancer research* 74: 3418-3428).

LAG3 is constitutively expressed at a low level on resting regulatory T cells (Tregs), and at a higher level on activated Tregs. LAG3 expression is required for Treg differentiation and maximal suppressive activity (Huang C T et al., (2004) *Immunity* 21: 503-513), and MHC class II binding to LAG3 on Tregs has been shown to inhibit DC activation and maturation (Liang B et al., (2008) *Journal of immunology* 180: 5916-5926).

As mentioned above, LAG3 generally inhibits the immune system, down-regulating the immune responses. LAG3 expression has been found to strongly correlate with infection severity, and high LAG3 level on tumor-infiltrating T cells may contribute to escape mechanism by tumor cells (Richter K et al., (2010) *International immunology* 22: 13-23). In another aspect, LAG3 insufficiency may lead to onset or exacerbation of autoimmune diseases.

Antagonistic anti-LAG3 antibodies such as MK-4280 (Merck, a humanized IgG4 antibody) and BMS-986016 (Relatlimab, Bristol-Myers Squibbm, a fully human IgG4 antibody), alone or in combination with anti-PD-1/anti-PD-L1, have been developed and clinically tested for the treatment of solid cancers, including breast cancers, renal cell carcinoma, melanoma, pancreas cancer, non-small cell lung cancer, glioblastoma, and gastric cancer. Antagonistic anti-LAG3 antibodies may also target and eliminate LAG3+ immune cells in patient lesions with autoimmune diseases. For example, GSK2831781 (GlaxoSmithKline) is now in clinical trial for patients with plaque psoriasis (Andrews L P et al., (2017) *Immunological Reviews*. 276(1): 80-96).

In view of LAG3's role in immune system regulation, there remains a need for more anti-LAG3 antibodies with improved pharmaceutical characteristics.

Citation or identification of any document in this application is not an admission that such document is available as prior art to the present invention.

SUMMARY OF THE INVENTION

The present disclosure provides an isolated monoclonal antibody, for example, a mouse, human, chimeric or humanized monoclonal antibody, or an antigen-binding portion thereof that binds to LAG3 (e.g., the human LAG3, and monkey LAG3). The antibody or the antigen-binding portion thereof of the disclosure has comparable binding activity/affinity to human/monkey LAG3, comparable or higher blocking activity on LAG3-MHC II interaction, higher promoting effect on T cell activation, and comparable or higher in vivo anti-tumor effect, as compared to the prior art antibodies such as BMS-986016.

The antibody or the antigen-binding portion thereof of the disclosure can be used for a variety of applications, including detection of the LAG3 protein, and treatment of LAG3 associated diseases.

Accordingly, in one aspect, the disclosure pertains to an isolated monoclonal antibody (e.g., a humanized antibody), or an antigen-binding portion thereof, that binds LAG3, having a heavy chain variable region which may comprises a VH CDR1 region, a VH CDR2 region and a VH CDR3 region, wherein the VH CDR1 region, the VH CDR2 region and the VH CDR3 region may comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 1, 2 and 3, respectively; (2) SEQ ID NOs: 1, 2 and 4, respectively; or (3) SEQ ID NOs: 21, 22 and 23, respectively; and/or a light chain variable region that may comprise a VL CDR1 region, a VL CDR2 region and a VL CDR3 region, wherein the VL CDR1 region, the VL CDR2 region, and the VL CDR3 region may comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 5, 6 and 7, respectively; (2) SEQ ID NOs: 5, 6 and 8, respectively; or (3) SEQ ID NOs: 24, 25 and 26, respectively.

In certain embodiments, the isolated monoclonal antibody, or the antigen-binding portion thereof, of the present disclosure may comprise a VH CDR1 region, a VH CDR2 region, a VH CDR3 region, a VL CDR1 region, a VL CDR2 region and a VL CDR3 region which may comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 1, 2, 3, 5, 6 and 7, respectively; (2) SEQ ID NOs: 1, 2, 4, 5, 6 and 8, respectively; or (3) 18, 19, 20, 21, 22 and 23, respectively.

The isolated monoclonal antibody, or the antigen-binding portion thereof, of the present disclosure may comprise a heavy chain variable region that may comprise an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID NOs: 9, 10, 11, 12, 13, 14, 27, 28, 29 or 30.

The isolated monoclonal antibody, or the antigen-binding portion thereof, of the present disclosure may comprise a light chain variable region that may comprise an amino acid sequence having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in SEQ ID NOs: 15, 16, 17, 18, 19, 20, 31, 32, 33 or 34.

In certain embodiments, the isolated monoclonal antibody, or the antigen-binding portion thereof, of the present disclosure may comprise a heavy chain variable region and a light chain variable region which may comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 9 and 15, respectively; (2) SEQ ID NOs: 10 and 16, respectively; (3) SEQ ID NOs: 11 and 17, respectively; (4) SEQ ID NOs: 11 and 19, respectively; (5) SEQ ID NOs: 12 and 17, respectively; (6) SEQ ID NOs: 12 and 19, respectively; (7) SEQ ID NOs: 13 and 18, respectively; (8) SEQ ID NOs: 13 and 20, respectively; (9) SEQ ID NOs: 14 and 20, respectively; (10) SEQ ID NOs: 27 and 31, respectively; (11) SEQ ID NOs: 28 and 32, respectively; (12) SEQ ID NOs: 29 and 33, respectively; (13) SEQ ID NOs: 29 and 34, respectively; (14) SEQ ID NOs: 30 and 33, respectively; or (15) SEQ ID NOs: 30 and 34, respectively.

The isolated monoclonal antibody, or the antigen-binding portion thereof, of the present disclosure may further comprise a heavy chain constant region and/or a light chain constant region. The heavy chain constant region may be a IgG4 heavy chain constant region, such as human IgG4 heavy chain constant region, or more specifically human IgG4 heavy chain constant region with S228P mutation, having e.g., the amino acid sequence set forth in SEQ ID NO: 35, or a fragment thereof. The light chain constant region may be kappa light chain constant region, such as human kappa light chain constant region having e.g., the amino acid sequence set forth in SEQ ID NO: 36, or a fragment thereof. The S228P mutation in the IgG4 heavy chain constant region may help to enhance the structure stability of IgG4 isotyped antibodies. The N terminus of the heavy chain constant region may be linked to the C terminus of the heavy chain variable region, and the N terminus of the light chain constant region may be linked to the C terminus of the light chain variable region.

In certain embodiments, the heavy chain constant region may be a IgG1 heavy chain constant region, such as human IgG1 heavy chain constant region, and the light chain constant region may be kappa light chain constant region, such as human kappa light constant region.

The antibody of the present disclosure in certain embodiments may comprise or consist of two heavy chains and two light chains connected by disulfide bonds, wherein each heavy chain may comprise the heavy chain constant region, heavy chain variable region or VH CDR sequences mentioned above, and each light chain may comprise the light chain constant region, light chain variable region or VL CDR sequences mentioned above, wherein the C-terminus of the heavy chain variable region is linked to N-terminus of the heavy chain constant region, and the C-terminus of the light chain variable region is linked to the N-terminus of the light chain constant region, wherein the antibody binds to LAG3. The antibody of the disclosure can be a full-length antibody, for example, of an IgG1, IgG2 or IgG4 isotype. The antibody of the disclosure may contain a kappa constant region. The antibody or the antigen-binding portion thereof of the present disclosure in other embodiments may be a single chain antibody, or consists of antibody fragments, such as Fab or F(ab')$_2$ fragments.

The antibody, or the antigen-binding portion thereof, of the present disclosure may bind specifically to human and monkey LAG3, block LAG3-MHC II interaction, promote T cell activation, and provide in vivo anti-tumor effect. The antibody, or the antigen-binding portion thereof, of the present disclosure may also provide in vivo anti-inflammatory effect and can be used in treatment or alleviation of inflammatory diseases such as autoimmune diseases.

The disclosure also provides an immuneconjugate comprising an antibody or an antigen-binding portion thereof of the disclosure, linked to a therapeutic agent, such as a cytotoxin or an anti-tumor agent. The disclosure also provides a bispecific molecule comprising an antibody, or antigen-binding portion thereof, of the disclosure, linked to a second functional moiety (e.g., a second antibody) having a different binding specificity than said antibody, or antigen-binding portion thereof. In another aspect, the antibody or the antigen-binding portion thereof of the present disclosure can be made into part of a chimeric antigen receptor (CAR) or a T cell receptor (TCR). The disclosure further provides an immune cell with the CAR or TCR mentioned above, such as a T cell and a NK cell.

Compositions comprising an antibody, or an antigen-binding portion thereof, an immunoconjugate, a bispecific molecule, or an immune cell of the disclosure, and a pharmaceutically acceptable carrier, are also provided.

Nucleic acid molecules encoding the antibody, or the antigen-binding portion thereof, of the disclosure are also encompassed by the disclosure, as well as expression vectors comprising such nucleic acids and host cells comprising such expression vectors. A method for preparing an anti-LAG3 antibody or an antigen-binding portion thereof using the host cell comprising the expression vector is also provided, comprising steps of (i) expressing the antibody or antigen-binding portion thereof in the host cell and (ii) isolating the antibody or antigen-binding portion from the host cell or its cell culture.

In another aspect, the disclosure provides a method for enhancing an immune response in a subject, comprising administering to the subject a therapeutically effective amount of the antibody, or the antigen-binding portion thereof, of the disclosure. In certain embodiments, the method comprises administering a composition, or a bispecific molecule of the disclosure. The antibody or antigen-binding portion thereof used in the immune response enhancement may be of an IgG4 isotype.

In another aspect, the disclosure provides a method for treating or reducing the progression of a tumor in a subject in need thereof, comprising administering to the subject a therapeutically effective amount of the antibody, or the antigen-binding portion thereof, of the disclosure. The cancer may be a solid tumor, including, but not limited to, colon adenocarcinoma, breast cancers, renal cell carcinoma, melanoma, pancreas cancer, non-small cell lung cancer, glioblastoma, and gastric cancer. The antibody or antigen-binding portion thereof used in cancer treatment may be of an IgG4 isotype. In certain embodiments, the method comprises administering a composition, an expression vector, a bispecific molecule or an immunoconjugate of the disclosure. In certain embodiments, the subject may be further administered with at least one additional anti-cancer antibody or antigen-binding portion thereof, such as an anti-PD-1 antibody, an anti-PD-L1 antibody, an anti-STAT3 antibody, an anti-ROR1 antibody, an anti-TIM3 antibody, and/or an anti-CTLA-4 antibody. In yet another embodiment, the subject may be further administered with a cytokine (e.g., IL-2 and/or IL-21), or a costimulatory antibody (e.g., an anti-CD137 and/or anti-GITR antibody). In another embodiment, the subject may be further administered with a chemotherapeutic agent, which may be a cytotoxic agent. The antibody or antigen-binding portion thereof of the present disclosure may be, for example, a mouse, human, chimeric or humanized antibody or antigen-binding portion thereof.

In another aspect, the disclosure provides a method for treating or alleviating an infectious disease in a subject in need thereof, comprising administering to the subject a therapeutically effective amount of the antibody, or the antigen-binding portion thereof, of the disclosure. The infectious disease may be a disease caused by viral, bacterial, fungal or *mycoplasma* infection. The antibody or antigen-binding portion thereof used in the infectious disease treatment may be of an IgG4 isotype. In certain embodiments, the method comprises administering a composition, an expression vector, a bispecific molecule, or an immunoconjugate of the disclosure. In certain embodiments, the subject may be further administered with at least one an anti-infective agent, such as an anti-viral agent, an anti-bacterial agent, an anti-fungal agent, or an anti-*mycoplasma* agent.

In another aspect, the disclosure provides a method for treating or alleviating an autoimmune disease in a subject in need thereof, comprising administering to the subject a therapeutically effective amount of the antibody, or the antigen-binding portion thereof, of the disclosure. The antibody or antigen-binding portion thereof for treatment of an autoimmune disease may be of an IgG1 isotype, and the IgG1 heavy chain constant region may be further engineered to induce an enhanced antibody-dependent cellular cytotoxicity (ADCC) and/or an enhanced complement-dependent cytotoxicity (CDC). In certain embodiments, the method comprises administering a composition, an expression vector, a bispecific molecule, or an immune cell of the disclosure. In certain embodiments, the antibody or antigen-binding portion thereof, a composition, an expression vector, a bispecific molecule, or an immune cell of the disclosure may be administered at or around the lesions. In certain embodiments, the subject may be further administered with at least one anti-inflammatory agent, such as an IL-2 inhibitor, an IL-17 inhibitor (e.g., Taltz® Ixekizumab, bimekizumab), and/or anti-IL-23 inhibitor for plaque psoriasis treatment.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
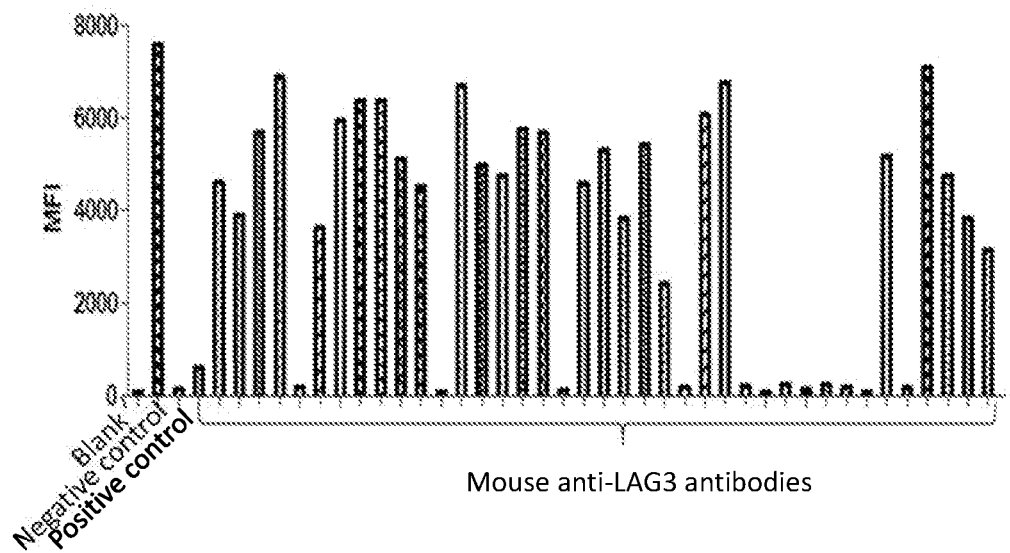
FIG. 1 shows the inhibitory effect of mouse anti-LAG3 antibodies on LAG3 binding to MHCII on Daudi cells.

To ensure that the present disclosure may be more readily understood, certain terms are first defined. Additional definitions are set forth throughout the detailed description.

The term "LAG3" refers to lymphocyte activation gene 3. The term "LAG3" comprises variants, isoforms, homologs, orthologs and paralogs. For example, an antibody specific for a human LAG3 protein may, in certain cases, cross-react with a LAG3 protein from a species other than human, such as monkey. In other embodiments, an antibody specific for a human LAG3 protein may be completely specific for the human LAG3 protein and exhibit no cross-reactivity to other species or of other types, or may cross-react with LAG3 from certain other species but not all other species.

The term "human LAG3" refers to an LAG3 protein having an amino acid sequence from a human, such as the amino acid sequence of human LAG3 having a Genbank accession number of NP_002277.4 or encoded by the nucleotide sequence set forth in SEQ ID NO: 37. The term "monkey or rhesus LAG3" refers to monkey LAG3 protein having an amino acid sequence from monkey, such as the amino acid sequence of monkey LAG3 having a Genbank accession number of XP_001108923.1 or encoded by the nucleotide sequence set forth in SEQ ID NO: 38. The term "mouse LAG3" refers to an LAG3 protein having an amino acid sequence from mouse, such as the amino acid sequence of mouse LAG3 having a Genbank accession number of NP_032505.1 or encoded by the nucleotide sequence set forth in SEQ ID NO: 39.

The term "antibody" as referred to herein includes IgG, IgA, IgD, IgE and IgM whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a LAG3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG3 protein is substantially free of antibodies that specifically bind antigens other than LAG3 proteins). An isolated antibody that specifically binds a human LAG3 protein may, however, have cross-reactivity to other antigens, such as LAG3 proteins from other species. Moreover, an isolated antibody can be substantially free of other cellular material and/or chemicals.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human LAG3" is intended to refer to an antibody that binds to human LAG3 protein (and possibly a LAG3 protein from one or more non-human species) but does not substantially bind to non-LAG3 proteins. Preferably, the antibody binds to human LAG3 protein with "high affinity", namely with a $K_D$ of $5.0 \times 10^{-8}$ M or less, more preferably $1.0 \times 10^{-8}$ M or less, and more preferably $5.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "antibody-dependent cellular cytotoxicity", "antibody-dependent cell-mediated cytotoxicity" or "ADCC," as used herein, refers to a mechanism of cell-mediated immune defense whereby an effector cell of the immune system actively lyses a target cell, such as a tumor cell or an immune cell, whose membrane-surface antigens have been bound by antibodies such as anti-LAG3 antibodies.

The term "complement-dependent cytotoxicity" or "CDC" generally refers to an effector function of IgG and IgM antibodies, which trigger classical complement pathway when bound to a surface antigen, inducing formation of a membrane attack complex and target cell lysis. The antibody of the present disclosure, by binding to LAG3, induces CDC against cancer cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or antigen-binding portion thereof of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

The term "antagonistic LAG3 antibody" refers to an anti-LAG3 antibody that may block or inhibit the LAG3 signaling induced by LAG3 binding to its ligand such as MHC II. The antagonistic LAG antibody may promote T cell activation to release cytokines and enhance immune responses.

Various aspects of the disclosure are described in further detail in the following subsections.

The antibody or the antigen-binding portion thereof of the disclosure has comparable binding activity/affinity to human/monkey LAG3, and comparable or higher blocking activity on LAG3-MHC II interaction, as compared to the prior art antibodies such as BMS-986016.

More importantly, the antibody or the antigen-binding portion thereof of the disclosure may have higher promoting effect on T cell activation than the prior art antibodies such as BMS-986016, and comparable or even higher in vivo anti-tumor effect as compared to the prior art antibodies such as BMS-986016 and MK-4280.

Preferred antibodies of the disclosure are monoclonal antibodies. Additionally or alternatively, the antibodies can be, for example, mouse, chimeric or humanized monoclonal antibodies.

An exemplary antibody of the disclosure is the monoclonal antibody structurally and chemically characterized as described below and in the following Examples.

The heavy chain variable region CDRs and the light chain variable region CDRs in Table 1 have been defined by the Kabat numbering system. However, as is well known in the art, CDR regions can also be determined by other systems such as Chothia, IMGT, AbM, or Contact numbering system/method, based on heavy chain/light chain variable region sequences.

The SEQ ID numbers of the amino acid sequences of the heavy/light chain variable regions and CDRs are listed in Table 1, with some antibodies share the same $V_H$ or $V_L$ sequences.

The exemplary antibody of the disclosure may contain a heavy chain constant region and/or a light chain constant region. The heavy chain constant region may be an IgG4 or IgG1 heavy chain constant region, depending on the diseases/conditions to treat. The IgG4 heavy chain constant region may be a human IgG4 heavy chain constant region, e.g., with S228P mutation, having e.g., the amino acid sequence set forth in SEQ ID NO: 35. The S228P mutation in the IgG4 constant region may help to enhance the structure stability of IgG4 isotyped antibodies. The light chain constant region may be a kappa constant region, such as a human kappa constant region, having e.g., the amino acid sequence of SEQ ID NO: 36.

The $V_H$ and $V_L$ sequences (or CDR sequences) of other anti-LAG3 antibodies which bind to human LAG3 can be "mixed and matched" with the $V_H$ and $V_L$ sequences (or CDR sequences) of the anti-LAG3 antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another anti-LAG3 antibody, wherein the antibody specifically binds human LAG3.

TABLE 1

Amino acid sequence ID numbers of heavy/light chain variable regions and CDRs

| Antibody ID | SEQ ID NO. | | | | | | | |
|---|---|---|---|---|---|---|---|---|
| | HV-CDR1 | HV-CDR2 | HV-CDR3 | HV | LV-CDR1 | LV-CDR2 | LV-CDR3 | LV |
| mouse and chimeric 101F4 | 1 | 2 | 3 | 9 | 5 | 6 | 7 | 15 |
| 101F4H0L0 | 1 | 2 | 3 | 10 | 5 | 6 | 7 | 16 |
| 101F4H2L2 | 1 | 2 | 3 | 11 | 5 | 6 | 7 | 17 |
| 101F4H2L3 | 1 | 2 | 3 | 11 | 5 | 6 | 7 | 19 |
| 101F4H3L2 | 1 | 2 | 3 | 12 | 5 | 6 | 7 | 17 |
| 101F4H3L3 | 1 | 2 | 3 | 12 | 5 | 6 | 7 | 19 |
| 101F4H2L2-8 | 1 | 2 | 4 | 13 | 5 | 6 | 8 | 18 |
| 101F4H2L3-8 | 1 | 2 | 4 | 13 | 5 | 6 | 8 | 20 |
| 101F4H3L3-8 | 1 | 2 | 4 | 14 | 5 | 6 | 8 | 20 |
| mouse and chimeric 134G10 | 21 | 22 | 23 | 27 | 24 | 25 | 26 | 31 |
| 134G10H0L0 | 21 | 22 | 23 | 28 | 24 | 25 | 26 | 32 |
| 134G10H2L2 | 21 | 22 | 23 | 29 | 24 | 25 | 26 | 33 |
| 134G10H2L3 | 21 | 22 | 23 | 29 | 24 | 25 | 26 | 34 |
| 134G10H3L2 | 21 | 22 | 23 | 30 | 24 | 25 | 26 | 33 |
| 134G10H3L3 | 21 | 22 | 23 | 30 | 24 | 25 | 26 | 34 |

In another embodiment, an antibody of the disclosure, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-LAG3 antibody, wherein the antibody specifically binds human LAG3.

In yet another embodiment, the antibody, or antigen binding portion thereof, includes the heavy chain variable CDR2 region of anti-LAG3 antibody combined with CDRs of other antibodies which bind human LAG3, e.g., CDR1 and/or CDR3 from the heavy chain variable region, and/or CDR1, CDR2, and/or CDR3 from the light chain variable region of a different anti-LAG3 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIA-journal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-LAG3 antibody and at least the CDR3 of the heavy and/or light chain variable region of the anti-LAG3 antibody, or the CDR3 of the heavy and/or light chain variable region of another anti-LAG3 antibody, wherein the antibody is capable of specifically binding to human LAG3. These antibodies preferably (a) compete for binding with LAG3; (b) retain the functional characteristics; (c) bind to the same epitope; and/or (d) have a similar binding affinity as the anti-LAG3 antibody of the present disclosure. In yet another embodiment, the antibodies further may comprise the CDR2 of the light chain variable region of the anti-LAG3 antibody, or the CDR2 of the light chain variable region of another anti-LAG3 antibody, wherein the antibody is capable of specifically binding to human LAG3. In another embodiment, the antibodies of the disclosure may include the CDR1 of the heavy and/or light chain variable region of the anti-LAG3 antibody, or the CDR1 of the heavy and/or light chain variable region of another anti-LAG3 antibody, wherein the antibody is capable of specifically binding to human LAG3.

In another embodiment, an antibody of the disclosure comprises a heavy and/or light chain variable region sequences of CDR1, CDR2 and CDR3 sequences which differ from those of the anti-LAG3 antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or
(d) the light chain variable region CDR1, and/or CDR2, and/or CDR3 sequences comprise the sequence(s) listed in Table 1 above; and/or conservative modifications thereof; and
(e) the antibody specifically binds human LAG3.

The antibody of the present disclosure possesses one or more of the following functional properties described above, such as high affinity binding to human LAG3.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-LAG3 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) Nature 321:522-525; Queen et al., (1989) Proc. Natl. Acad. See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) J. Mol. Biol. 227:776-798; and Cox et al., (1994) Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-LAG3 monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha(1,6)$-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application Ser. No. 60/836,998, filed on Aug. 11, 2006. PCT Publication WO 99/54342 describes cell lines engineered to express glycoprotein-modifying glycosyl transferases (e.g., $\beta(1,4)$-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-LAG3 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-LAG3 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the LAG3 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) Science 242:423-426; Huston et al., (1988) Proc. Natl. Acad. Sci. USA 85:5879-5883; McCafferty et al., (1990) Nature 348:552-554).

Monoclonal antibodies (mAbs) of the present disclosure can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051, 081; WO 07/059,404; WO 08/083,312; and WO 08/103,693; U.S. Patent Publications 20060024317; 20060004081; and 20060247295; the disclosures of which are incorporated herein by reference.

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-LAG3 binding specificity, a third specificity. The third specificity can be for PD-1 or CTLA-4, to enhance immune responses. Alternatively, the third specificity may be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, LAG3, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Chimeric Antigen Receptor

The present disclosure further provides a chimeric antigen receptor containing an anti-LAG3 scFv, wherein the anti-LAG3 scFv contains the heavy/light chain variable regions and/or CDRs of the disclosure.

The chimeric antigen receptor of the disclosure may comprise (a) an extracellular antigen binding domain containing an anti-LAG3 scFv; (b) a transmembrane domain; and (c) an intracellular domain containing a signaling domain and/or a costimulatory domain.

In another aspect, the present disclosure provides a pharmaceutical composition comprising one or more antibodies or antigen-binding portions thereof, one or more nucleic acids encoding the antibodies or antigen-binding portions thereof, one or more immunoconjugates, one or more immune cells carrying the CARs, and/or one or more bispecific molecules of the present disclosure formulated together with a pharmaceutically acceptable carrier. The composition may optionally contain one or more additional pharmaceutically active ingredients, such as another antibody or a drug, such as an ant-tumor antibody, an anti-infectious antibody, an anti-inflammatory antibody, or an antibody for enhancing immune response, or another non-antibody therapeutic agent, such as an anti-tumor agent, an anti-infectious agent, an anti-inflammatory agent, or a costimulatory agent. The pharmaceutical compositions of the disclosure also can be administered in a combination therapy with, for example, an anti-tumor agent, an anti-infectious agent, an anti-inflammatory agent, or a costimulatory agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-LAG3 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-LAG3 antibody or antigen-binding portion thereof of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal. For the treatment of subjects with autoimmune disorders, a "therapeutically effective dosage" preferably alleviate inflammations by at least about 20%, more preferably by at least about 40%, even more preferably by at least about 60%, and still more preferably by at least about 80%, relative to untreated subjects, or totally eliminate inflammations.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374, 548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical compositions of the present disclosure have numerous in vitro and in vivo utilities, including, for example, treatment and/or prevention of cancers, inflammatory diseases, or infectious diseases, or more generally immune response enhancement in patients with cancers or infectious diseases, or immune cell reduce in lesions of patients with inflammatory diseases such as autoimmune diseases. The pharmaceutical compositions can be administered to human subjects, e.g., in vivo, to inhibit tumor growth, to reduce or eliminate pathogens, or alleviate autoimmune inflammations.

Given the ability of the pharmaceutical compositions of the disclosure to inhibit proliferation and survival of cancer cells, the disclosure provides methods for inhibiting growth of tumor cells in a subject in need thereof comprising administering to the subject a pharmaceutical composition of the disclosure such that growth of the tumor is inhibited in the subject. Non-limiting examples of tumors that can be treated by the pharmaceutical compositions of the disclosure include, but not limited to, colon adenocarcinoma, breast cancers, renal cell carcinoma, melanoma, pancreas cancer, non-small cell lung cancer, glioblastoma, and gastric cancer, original and/or metastatic. Additionally, the pharmaceutical compositions of the disclosure may also apply to refractory or recurrent malignancies whose growth may be inhibited by the compositions of the disclosure.

The pharmaceutical composition of the disclosure may be used to reduce or eliminate pathogens. Thus, the disclosure provides a method for treating an infectious disease, caused by a virus, a bacterium, a fungus or a *mycoplasma*, in a subject in need thereof, comprising administering to the subject the pharmaceutical composition of the disclosure.

The pharmaceutical compositions of the disclosure may be used to treat or alleviate inflammatory diseases. Thus, the present disclosure provides a method for treating an autoimmune disease in a subject in need thereof, comprising administering to the subject a pharmaceutical composition of the disclosure, especially at or around the lesions. The autoimmune disease may be plaque psoriasis.

These and other methods of the disclosure are discussed in further detail below.

In another aspect, the disclosure provides methods of combination therapy in which a pharmaceutical composition of the present disclosure is co-administered with one or more additional antibodies or non-antibody agents that are effective in inhibiting tumor growth in a subject. In one embodiment, the disclosure provides a method for inhibiting tumor growth in a subject comprising administering to the subject a pharmaceutical composition of the disclosure and one or more additional antibodies, such as an anti-TIM3 antibody, an anti- an anti-PD-L1 antibody, and anti-PD-1 antibody and/or an anti-CTLA-4 antibody. In certain embodiments, the subject is human. In certain embodiments, the pharmaceutical composition of the disclosure may be further combined with standard cancer treatments. For example, LAG3 signaling blockade can be combined with CTLA-4 and/or PD-1 blockade and also chemotherapeutic regimes. For example, a chemotherapeutic agent can be administered with the pharmaceutical composition of the disclosure, which may be a cytotoxic agent. For example, epitubicin, oxaliplatin, and 5-FU are administered to patients receiving anti-LAG3 therapy. Other therapies that may be combined with anti-LAG3 therapy includes, but not limited to, interleukin-2 (IL-2) administration, radiation, surgery, or hormone deprivation.

In another aspect, the disclosure provides methods of combination therapy in which a pharmaceutical composition of the present disclosure is co-administered with one or more additional antibodies or non-antibody agents that are effective in reducing or eliminating pathogens such as bacteria, viruses, fungi, and/or mycoplasmas. For example, the pharmaceutical composition of the disclosure may be administered with an anti-infectious agent, such as an anti-virus agent, an anti-bacterial agent, an anti-fungal agent, or an anti-*mycoplasma* agent.

In another aspect, the disclosure provides methods of combination therapy in which a pharmaceutical composition of the present disclosure is co-administered with one or more additional antibodies or non-antibody agents that are effective in treating or alleviating an autoimmune disorder, such as plaque psoriasis. For example, the pharmaceutical composition of the disclosure may be administered with an agent for treating an autoimmune disorder, such as an IL-2 inhibitor, an IL-17 inhibitor (e.g., Taltz® Ixekizumab, bimekizumab), and/or anti-IL-23 inhibitor for plaque psoriasis treatment.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Construction of HEK293A Cell Lines Stably Expressing Human, Monkey or Mouse LAG3

Cell lines stably overexpressing human, monkey or mouse LAG3 proteins were constructed using HEK293A cells (Cobioer, NJ, China). Briefly, human, monkey or mouse LAG3 cDNA sequences (SEQ ID NOs: 37, 38 and 39, respectively) were synthesized, and then subcloned into pLV-EGFP(2A)-Puro vectors (Beijing Inovogen, China) between the restriction sites EcoRI and XhoI. Lentiviruses were generated in HEK-293T cells (Cobioer, NJ, China) by cotransfection of pLV-EGFP(2A)-Puro-LAG3, psPAX and pMD2.G plasmids, according to the instruction in Lipofectamine 3000 kit (Thermo Fisher Scientific, US). Three days post cotransfection, the lentiviruses were harvested from the cell culture medium (DMEM, Cat #: SH30022.01, Gibco) with 10% FBS (Cat #: FND500, Excell)). The HEK293A cells were then infected with the lentiviruses to generate HEK293A cell lines stably expressing human, monkey or mouse LAG3, namely HEK293A/human LAG3, HEK293A/rh LAG3 and HEK293A/mouse LAG3 cells, respectively. Transfected HEK293A cells were cultured in medium (DMEM+10% FBS) containing 0.2 μg/ml puromycin (Cat #: A11138-03, Gibco) for 7 days. The expression of human LAG3 and monkey LAG3 proteins were confirmed by FACS using a commercially available anti-LAG3 antibody (PE-anti-human LAG3, Biolegend, US, Cat #: 369205). Similarly, the expression of mouse LAG3 proteins was confirmed by FACS using a commercially available anti-mouse LAG3 antibody (PE-anti-mouse LAG3, Biolegend, US, Cat #: 125207).

Example 2 Generation of Hybridoma Cell Lines Producing Monoclonal Mouse Antibodies Against Human LAG3

Murine anti-human LAG3 monoclonal antibodies (mAbs) were generated using the conventional hybridoma fusion technology with some modifications.

Immunization

Thirteen BALB/c mice (Beijing Vital River Laboratory Animal Technology Co., Ltd, Beijing, China) were injected with recombinant human LAG3(ECD)-hFc (Sino Biological, CN, Cat #:16498-H02H) and recombinant monkey LAG3(ECD)-hFc (ACRO, CN, Cat #: LA3-05252) following the scheme in Table 2 below. The human LAG3(ECD)-hFc and monkey LAG3(ECD)-hFc proteins were emulsified by sonication with an equal volume of Complete Freund's Adjuvant (SIGMA, USA, Cat #: F5881-10*10ML), Incomplete Freund's Adjuvant (SIGMA, USA, Cat #: F5506-6*10ML), or PBS.

TABLE 2

| | Immunization scheme | | | | |
|---|---|---|---|---|---|
| Day | Primary 0 | 1st Boost 14 | 2nd Boost 28 | 3rd Boost 42 | Final Boost 56 |
| Protein and dose | Human LAG3(ECD)-hFc (50 μg/mouse) | Human LAG3(ECD)-hFc (50 μg/mouse) | rh LAG3(ECD)-hFc (50 μg/mouse) | Human LAG3(ECD)-hFc (50 μg/mouse) | rh LAG3(ECD)-hFc (25 ug/mouse) + Human LAG3(ECD)-hFc (25 μg/mouse) |
| Adjuvant | Complete Freund's | Incomplete Freund's | Incomplete Freund's | Incomplete Freund's | PBS |
| Way of immunization | i.p. | i.p. | i.p. | i.p. | i.v. |

One week after each boost, 50 μl of murine serum was collected from each mouse for titer determination by ELISA using the recombinant human LAG3(ECD)-his (Sino Biological, CN, Cat #:16498-H08H), monkey LAG3(ECD)-hFc (ACRO, CN, Cat #: LA3-05252), and mouse LAG3(ECD)-his (Sino Biological, CN, Cat #: 53069-M08H). Titer determination was also done by FACS using HEK293A overexpressing human LAG3, monkey LAG3 or mouse LAG3 as prepared in Example 1.

Based on the ELISA and FACS analysis results after the final boost, ten mice with highest serum titers were chosen for hybridoma cell line generation.

Generation of Hybridoma Cell Lines

Hybridoma cell lines were generated using the conventional hybridoma fusion technology with minor modifications.

Four days after the final boost, mice were sacrificed, and spleens were collected and prepared as single cell suspensions in PBS. The spleenocytes were washed for three times with DMEM medium (Hyclone, Cat #: SH30243.01B). Viable myeloma cells SP2/0 (ATCC, CRL-1581) at the log-phase were mixed with the murine spleenocytes in a ratio of 1:4. The cells were then washed twice and then cell fusion was performed with PEG (Sigma, Cat #: P7181). The post-fusion cells were washed with DMEM medium for three times and suspended in cell growth medium (RPMI medium 1640 (Gibco, Cat #: C22400500CP)) supplemented with 10% FBS and 1× HAT (Sigma, H0262). The cell suspension was plated onto 96 well cell culture plates, 200 μl per well ($5 \times 10^4$ cells/well), and incubated in a 37° C. humidified 5% $CO_2$ incubator for 7 days. Then, the growth medium was replaced by fresh growth medium supplemented with 10% FBS+1× HT. Two to three days later, the hybridoma cells were screened by ELISA and FACS.

Screening of Hybridoma Cell Lines by ELISA

High-throughput ELISA binding assay was firstly used to screen for hybridoma clones producing monoclonal antibodies binding to human LAG3(ECD)-his (Sino Biological, CN, Cat #:16498-H08H). The clones producing human LAG3 binders were further tested for their abilities to cross-react with monkey or mouse LAG3, using rhesus LAG3(ECD)-hFc (ACRO, CN, Cat #: LA3-05252) and mouse LAG3(ECD)-his (Sino Biological, CN, Cat #:53069-M08H).

With the ELISA assays, 211 hybridoma clones were identified to have specific binding to both human and monkey LAG3 proteins.

Screening of Hybridoma Cell Lines by FACS

The 211 hybridoma clones were further screened for their binding capacities to human, rhesus or mouse LAG3 proteins expressed on HEK293A cells, using the HEK293A/human LAG3 cells, HEK293A/rh LAG3 cells and HEK293A/mouse LAG3 cells as prepared in Example 1.

Based on the FACS screening, 78 positive clones were obtained that displayed high binding capacity to both HEK293A/human LAG3 and HEK293A/rh LAG3 cells.

Subcloning of Hybridoma Clones Producing Anti-LAG3 Antibodies

The 78 hybridoma clones were subject to 2 rounds of subcloning. During the subcloning, multiple subclones (n>3) from each parent clone were selected and confirmed by ELISA and FACS assays as described above. The subclones selected through this process were defined as hybridoma cells producing monoclonal antibodies. Finally, 47 subclones (one subclone from each parent clone) having high binding capacity to both human and monkey LAG3 were obtained.

Example 3 Mouse Anti-LAG3 Antibodies Inhibited Human LAG3 Binding to MHC II on Daudi Cells To test the abilities of the clones to inhibit binding of LAG-3 to MHC Class II molecules, an in vitro binding assay was performed in which a LAG-3 fusion protein, comprising an human LAG-3 extracellular domain fused to human Fc (hLAG-3-hIg, Sino Biological, CN, Cat #:16498-H02H), was cultured with Daudi cells, which expressed human MHC Class II molecules.

Briefly, 100 µl of the cell culture medium collected from each of the 47 hybridoma cells was added with 10 µg/ml hLAG-3-hIg fusion protein. The mixtures were incubated for 20 minutes at room temperature prior to addition of $2\times10^5$ Daudi cells. The mixtures were further incubated at 4° C. for 30 minutes. The cells were pelleted (five minutes, 300×g), washed twice with 1×PBS buffer (137 mM NaCl, 2.7 mM KCl, 10 mM $Na_2HPO_4$, 2 mM $KH_2PO_4$, PH7.4), and incubated with a recombinant PE-labeled F(ab')2 anti-hIgG Fc (1:200, Life Technologies, USA, Cat #: H10104) at 4° C. for 30 minutes. The cells were washed by PBS once, and tested for LAG-3-hIg binding with a FACS calibur flow cytometer (BD Bioscience). The blank well was not added with hLAG-3-hIg, and hLAG-3-hIg with Hel (LifeTein, USA, Cat #: LT12031) were used as the negative control. The reference antibody BMS-986016 (referred to as BMS, prepared using the amino acid sequences disclosed in EP 2320940B1 with human IgG4 (S228P)/kappa constant regions) plus hLAG-3-hIg were used as the positive control.

The results were summarized in FIG. 1, showing that BMS can completely block the binding of the LAG3 fusion proteins to MHC II complex on Daudi cells. Among the tested mouse anti-hLAG3 antibodies, there were totally 12 clones that completed blocked LAG3-MHC II binding.

Example 4 Purification and Isotype Determination of Mouse Anti-LAG3 Monoclonal Antibodies The 12 clones with LAG3-MHCII blocking activities were selected for further characterization. Firstly, the monoclonal mouse antibodies were purified. Briefly, hybridoma cells of each subclone were grown in T175 cell culture flasks each having 100 ml of fresh serum-free medium (Gibco, US, Cat #: 12045-076) with 1% HT supplement (Gibco, Cat #: 11067-030). Cell cultures were kept for 10 days in an incubator with 5% $CO_2$ at 37° C. Cell cultures were collected, followed by centrifugation at 3500 rpm for 5 minutes and then subjected to filtration using a 0.22 µm membrane to remove cell debris. Monoclonal mouse antibodies were then purified using a pre-equilibrated Protein-A affinity column (GE, USA, Cat #: 17040501) and eluted with elution buffer (20 mM citric acid, pH3.0-pH3.5). Then, antibodies were kept in PBS buffer (pH 7.0), and their concentrations were determined using a NanoDrop instrument.

The isotype of each purified antibody was determined by using the Rapid Isotyping Kit with Kappa and Lambda-Mouse (Thermal, USA, Cat #: 26179) and Mouse Monoclonal Antibody Isotyping Reagents (Sigma, USA, Cat #: IS02-1KT), following the manufacturer's manuals.

Most clones, including 101F4, produced IgG1/kappa antibodies, while 134G10 produced IgG2a/kappa antibodies. The expression titer for 134G10 and 101F4 were 8.6 mg/L and 3.4 mg/, respectively.

Example 5 Purified Mouse Anti-LAG3 Monoclonal Antibodies Bound to Human and Monkey LAG3

The purified mouse anti-LAG3 monoclonal antibodies were firstly tested by ELISA assays for their binding capacities to recombinant human, monkey and mouse LAG3 proteins.

ELISA plates were coated with 50 µl of 500 ng/ml human LAG3(ECD)-his (Sino Biological, CN, Cat #:16498-H08H) at 4° C. overnight. The wells were blocked with 200 µl of blocking buffer (PBS containing 1% BSA, 1% goat serum, and 0.05% Tween 20) for 2 hours at room temperature, and then 100 µl of serially diluted anti-LAG3 antibodies (starting from 40 µg/ml) were added to each well and incubated for 1 hour at RT. Plates were washed for 3 times with PBST (PBS+0.05% Tween 20), added with Goat-anti-mouse IgG-HRP (Sigma, US, Cat #: A9309-1 ml) diluted 5000×, and incubated for 1 hour at RT. Plates were developed with freshly prepared Ultra-TMB (BD, US, Cat #:555214) for 5 minutes at RT. Absorbance was read on a SpectraMaxR i3X (Molecular Devies, US) at 450 nm.

Species-cross-reactivity of the 12 LAG3 mAbs to monkey or mouse LAG3 was further tested by direct ELISA. Briefly, 50 µl of 500 ng/ml monkey LAG3(ECD)-hFc (ACRO, CN, Cat #: LA3-05252) or mouse LAG3-his (Sino Biological, CN, Cat #:53069-M08H) was coated on 96-well ELISA plates followed by incubation with 100 µl of serially diluted anti-LAG3 antibodies (starting from 40 µg/ml). Goat anti-mouse IgG conjugated with HRP (Sigma, US, Cat #: A9309-1 ml) was added then. BMS-986016 was used as the positive control.

$EC_{50}$ values for two representative antibodies and the reference antibody were summarized in Table 3. The data showed that all the 12 antibodies of the disclosure bound to human and monkey LAG3, but none of them cross-reacted with mouse LAG3.

TABLE 3

Binding capacity of representative mouse anti-LAG3 mAbs to human, monkey or mouse LAG3

| Antibody | ELISA ($EC_{50}$:M/L) | | |
|---|---|---|---|
|  | Human LAG3 (ECD)-his | Monkey LAG3 (ECD)-hFc | Mouse LAG3-his |
| BMS | 1.23E-9 | No binding | No binding |
| 101F4 | 4.0E-9 | 2.30E-9 | No binding |
| 134G10 | 1.92E-9 | 2.30E-10 | No binding |

Example 6 Mouse Anti-LAG3 Monoclonal Antibodies Bound to Human and Monkey LAG3 Proteins Expressed on HEK293A Cells To determine the binding capacities of the anti-LAG3 antibodies to human, monkey and mouse LAG3 proteins expressed on HEK293A cells, a cell-based binding assay by FACS was performed using the HEK293A cells stably overexpressing human, monkey and mouse LAG3 respectively, as generated in Example 1. Briefly, $10^5$ HEK293A cells in 50 μl PBS buffers were seeded into each well of the 96-well plates and then added with 50 μl of serially diluted anti-LAG3 antibodies (5-fold dilution, starting from 40 μg/ml). After incubated at 4° C. for 1 hour, plates were washed 3 times with PBST. Then, an APC coupled Goat Anti-Mouse IgG (BioLegend, US, Cat #: 405308) diluted 500× was added to the plates. After incubation at 4° C. for 1 hour, the plates were washed with PBS for 3 times and then cell fluorescence was monitored using a FACS machine (BD).

$EC_{50}$ values of 101F4, 134G10 and the reference antibody were summarized in Table 4 below. The data indicated that all of the mouse anti-LAG3 monoclonal antibodies of the disclosure showed high binding capacity to both human and monkey LAG3, but none bound to mouse LAG3.

TABLE 4

Binding activities of mouse anti-LAG3 antibodies to human, monkey and mouse LAG3

| Antibody | FACS($EC_{50}$: M/L) | | |
|---|---|---|---|
| | HEK-293A/human LAG3 | HEK-293A/rh LAG3 | HEK-293A/mouse LAG3 |
| BMS | 5.2E−11 | No binding | No binding |
| 101F4 | 3.6E−10 | 3.9E−10 | No binding |
| 134G10 | 8.6E−9 | 6.5E−9 | No binding |

Example 7 Epitope Binning

For epitope binning, a competitive ELISA assay was performed. Briefly, 96-well plates were coated with 5 μg/ml BMS, 50 μl per well, at 4° C. overnight. The wells were blocked with 200 μl of blocking buffer (PBS containing 1% BSA, 1% goat serum, and 0.05% Tween 20) for 2 hours at room temperature. Human LAG3(ECD)-his (Sino Biological, CN, Cat #:16498-H08H), 0.5 μg/mL, 50 μl per well, was added to the plates which were further incubated for 1 hour at RT. The ELISA plates were washed for 3 times with PBST, and then added and incubated with 100 μl of 1 μg/mL anti-LAG3 antibodies for 1 hour at RT. The ELISA plates were washed for 3 times with PBST, and then added and incubated with anti-mouse Fc-HRP (Sigma, US, Cat #: A9309-1MC) diluted at 1:20000 for 1 hour at RT. Plates were washed three times with PBS and developed with freshly prepared Ultra-TMB (Huzhou Yingchuang, CN, Cat #: TMB-S-003) for 5 minutes at RT. The absorbance was measured on SpectraMax microplate reader (Molecular Devices; US; SpectraMaxR i3X) at 450 nm (OD450).

Five mouse antibodies, including 101F4, competed with the reference antibody BMS for antigen binding, indicating that these antibodies and BMS bound to the same or similar epitopes. The remaining antibodies, including 134G10, did not compete with the reference antibody for antigen binding, indicating that these antibodies bound to different epitopes as compared to BMS.

Example 8 Purified Mouse Anti-LAG3 Antibodies Inhibited Binding of Human LAG3 to MHC II on Daudi Cells The capacities of the mouse anti-LAG3 antibodies to block LAG3 binding to MHC II molecules was tested by FACS as described in Example 3.

Briefly, 50 μl of mouse anti-LAG3 antibodies serially diluted with PBS (5-fold dilution, with highest concentration at 40 μg/ml) were incubated with 50 μl of 10 μg/ml hLAG-3-hIg fusion protein (Sino Biological, CN, Cat #:16498-H02H) for 20 minutes at room temperature. The mixtures were then added and incubated with $2 \times 10^5$ Daudi cells in 100 μl PBS buffer at 4° C. for 30 minutes. The cells were pelleted (three minutes, 400×g), washed twice with 1×PBS buffer and repelleted, and added and incubated with a recombinant PE-labeled F(ab')2 anti-hIgG Fc (1:200, Life Technologies, USA, Cat #: H10104) at 4° C. for 30 minutes, and washed once with 1×PBS. Analysis of LAG-3-mIg binding was carried out with the FACS flow cytometer (BD Bioscience). BMS was used as the positive control.

The data showed that all the antibodies of the disclosure blocked LAG3 binding to MHC II molecules. $EC_{50}$ values of 101F4, 134G10 and the reference antibody were summarized in Table 5 below, wherein the EC50 of 134G10 was lower than that of BMS.

TABLE 5

Blocking capacity of mouse anti-LAG3 antibodies on LAG3-MHCII interaction

| Antibody | Blocking assay $EC_{50}$(M/L) |
|---|---|
| BMS | 1.3E-8 |
| 101F4 | 1.3E-8 |
| 134G10 | 9.3E-9 |

Example 9 Mouse Anti-LAG3 Antibodies Promoted T Cell Activation

The role of mouse anti-LAG3 antibodies on APC-mediated T cell activation was studied by a mixed lymphocyte reaction (MLR) assay.

Briefly, PBMCs from a healthy human donor's blood sample were collected by density gradient centrifugation and re-suspended in RPMI1640 medium. PBMCs were cultured in a 37° C. incubator for 2 hours, and cells adhered to the container walls were collected as isolated monocytes. The monocytes were cultured with 100 ng/ml of recombinant human GM-CSF (R&D, US, Cat #: 7954-GM) and 100 ng/ml of recombinant human IL-4 (R&D, US, Cat #: 6507-IL) in RPMI1640 medium supplemented with 10% FBS in a plate. Three days later, half of the culture medium was replaced with fresh medium. On day 6 of culturing, the culture medium was replaced by fresh medium containing 100 ng/ml recombinant human GM-CSF, 100 ng/ml recombinant human IL-4, 10 ng/ml rhTNF-α (R&D, US, Cat #: 210-TA-100), 1000 U/ml rhIL-6 (R&D, US, Cat #: 7270-IL-025), 1 μg/ml PGE2 (TOCRIS, US, Cat #363-24-6) and 10 ng/ml of IL-1β (R&D, US, Cat #: 210-LB-025). The cells were cultured for another 2 days, to get dendritic cells (DCs).

PBMCs from another healthy human donor's blood sample were collected by density gradient centrifugation and then re-suspended in RPMI1640 medium. $CD4^+$ T cells were isolated from the PBMCs using Invitrogen Dynabeads Untouched Human CD4+ T cells isolation kit (Thermal Fisher Scientific, USA, Cat #: 11346D) according to the manufacturer's instructions.

The DCs from the first donor were seeded at $2.5 \times 10^4$ cells/well and the $CD4^+$ T cells from the second donor were seeded at $5 \times 10^4$ cells/well in 100 μl/well complete medium (90% DMEM+10% FBS) in a 96 well U-bottom plate.

Anti-LAG3 antibodies (final concentration at 100 µg/ml), or the control antibody Hel (LifeTein, US, Cat #: LT12031), 50 µl per well, were added to the cells, and the plate was further cultured for 72 h. IFN-γ concentration in the culture supernatants was determined by ELISA using an IFN-γ determination kit (R&D, US, Cat #: SIF50), according to the manufacturer's protocol. The assay was done in triplicate. The blank well contained only the isolated CD4+ T cells, and DCs plus CD4+ T cells and Hel were used as the negative control. DCs plus CD4+ T cells and the BMS at 100 µg/ml were used as the positive control.

Figure 2:
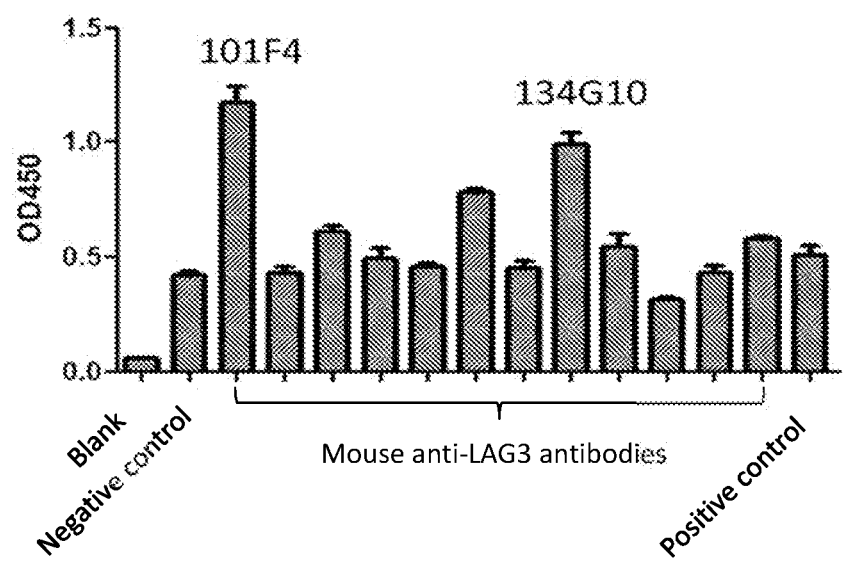
FIG. 2 shows the role of mouse anti-LAG3 antibodies in APC-mediated T cell activation, as measured by IFN-γ secretion.

As shown in FIG. 2, 6 antibodies, including 101F4 and 134G10, enhanced IFN-γ secretion by T cells, as compared to the Hel control, and highest IFN-γ levels were detected in wells treated with mouse anti-LAG3 antibodies 101F4 and 134G10.

Example 10 Expression and Purification of Chimeric 101F4 and 134G10 Antibodies

Antibodies 101F4 and 134G10 were further studied. The heavy/light chain variable region sequences of the two candidates were cloned from hybridoma cells using the standard PCR method with a set of degenerated primers as described in literatures (Juste et al., (2006), *Anal Biochem.* 1; 349(1):159-61) and then sequenced. The sequence ID numbers and sequences were summarized in Table 1 and Table 6. Expression vectors were constructed by inserting the sequence encoding the heavy chain variable region plus human IgG4 constant region (with a mutation S228P) or the sequence encoding the light chain variable region plus human kappa constant region (amino acid sequences of heavy chain constant region and light chain constant region set forth in SEQ ID NOs: 35 and 36, respectively) into pCDNA3.1 (Invitrogen, Carlsbad, USA) between the XhoI and BamHI restriction sites, wherein the C-terminus of the heavy chain variable region was linked to the N-terminus of the human IgG4 constant region, and the C-terminus of the light chain variable region was linked to the N-terminus of the human kappa constant region.

The expression vectors were PEI transfected into HEK-293F cells (Cobioer, NJ, China). In specific, HEK-293F cells were cultured in Free Style™ 293 Expression Medium (Gibco, Cat #: 12338-018) and transfected with the expression vectors using polyethyleneinimine (PEI) at a DNA:PEI ratio of 1:3, 1.5 µg of DNAs per millimeter of cell medium. Transfected HEK-293F cells were cultured in an incubator at 37° C. under 5% CO$_2$ with shaking at 120 RPM. After 10-12 days, culture supernatants were collected, and monoclonal antibodies were purified from the supernatants as described in Example 4. Chimeric antibodies are also referred to as "XX-CM" herein.

Example 11 Chimeric Anti-LAG3 Monoclonal Antibodies 101F4-CM and 134G10-CM Bound to Human and Monkey LAG3 Proteins Expressed on HEK293A Cells The chimeric anti-LAG3 antibodies 101F4-CM and 134G10-CM were characterized for their abilities of binding to HEK293A/human LAG3 cells, HEK293A/rh LAG3 cells, and HEK293A/mouse LAG3 cells, respectively, following the protocol described in Example 6.

Figure 3:
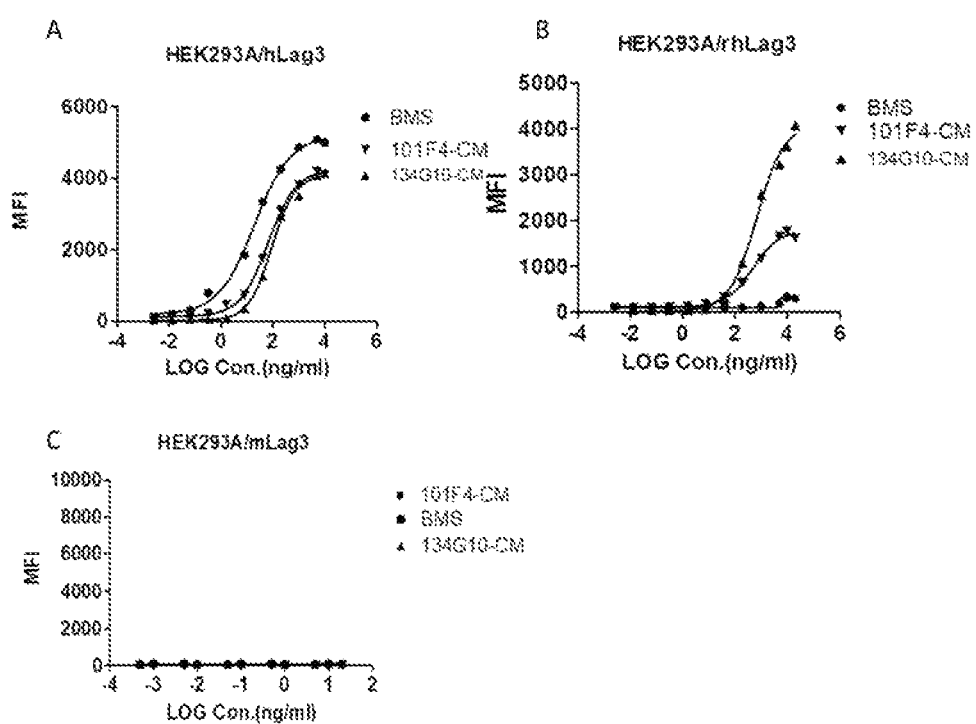
FIG. 3 shows the binding activities of chimeric 101F4 antibody (101F4-CM) and chimeric 134G10 antibody (134G10-CM) to HEK293A/human LAG3 (A), HEK293A/rhesus LAG3 (B), and HEK293A/mouse LAG3 (C).

As shown in FIG. 3, the two chimeric antibodies had high binding capacities to both human LAG3 (FIG. 3, A) and monkey LAG3 (FIG. 3, B), but did not bind mouse LAG3 (FIG. 3, C).

Example 12 Humanization of Exemplary Anti-LAG3 Antibodies

Based on the characterizations and assays described above, 101F4 and 134G10 were humanized and further studied. Humanization of the mouse 101F4 and 134G10 antibodies were conducted using the well-established CDR-grafting method as described in U.S. Pat. No. 5,225,539 (incorporated herein by reference) and below.

To select acceptor frameworks for humanization of mouse 101F4 and 134G10 antibodies, the light and heavy chain variable region sequences of 101F4 and 134G10 were blasted against the human immunoglobulin gene database in NCBI website (http://www.ncbi.nlm.nih.gov/igblast/). The human germline IGVH and IGVK with the highest homology to 101F4 and 134G10 were selected as the acceptor for humanization. For 101F4, the human heavy chain acceptor selected was IGHV1-24*01, and the human light chain acceptor selected was IGKV1-33*01. For 134G10, the human heavy chain acceptor selected was IGHV3-21*01, and the human light chain acceptor selected was IGKV4-1*01.

The three dimensional structures were simulated for variable domains of 101F4 and 134G10 in order to identify key framework residues that might be playing important roles in supporting CDR loop structures, and back mutations were designed based on this in humanized antibodies.

Based on the structural modeling above, 5 potential back-mutations (M70L, E72A, V24A, V68A and T98G) were identified for the heavy chain of 101F4 and 4 back-mutations (T69Q, F71Y, M4I and Y36F) were identified for the light chain of 101F4. And 2 potential back-mutations (G44R and S49G) were identified for the heavy chain of 134G10 and 3 back-mutations (D9S, G106A and S69T) for the light chain of 134G10.

As shown in Table 1, three humanized heavy chain variable regions and three humanized light chain variable regions were designed for both 101F4 and 134G10, generating a total of 5 humanized antibodies for each. The sequences and sequence ID numbers of the humanized antibodies were summarized in Table 1 and Table 6.

The sequence encoding the heavy chain variable region plus human IgG4 constant region (with a mutation S228P), and the sequence encoding the light chain variable region plus human kappa constant region (amino acid sequences of the heavy chain constant region and the light chain constant region set forth in SEQ ID NOs: 35 and 36, respectively) were chemically synthesized and then subcloned into GS expression vector (Invitrogen, USA) using the EcoR I/Xho I and Cla 1/Hind III restriction sites, respectively, wherein the C-terminus of the heavy chain variable region was linked to the N-terminus of the human IgG4 constant region (with a mutation S228P), and the C-terminus of the light chain variable region was linked to the N-terminus of the human kappa constant region. All expression constructs were confirmed by DNA sequencing. The EXPiCHO expression systems (Invitrogen, USA) were transfected with the heavy chain and light chain expressing vectors and transiently expressed 5 humanized 101F4 antibodies and 5 humanized 134G10 antibodies, following the protocol described in Example 10. The humanized antibodies were purified as described in Example 4.

Example 13 Characterization of Humanized 101F4 and 134G10 Antibodies

The humanized 101F4 and 134G10 antibodies were characterized for their abilities of binding to HEK293A/human LAG3 cells, HEK293A/rh LAG3 cells, and HEK293A/ mouse LAG3 cells, following the protocols as described in Example 6. The results were shown in FIG. 4.

These humanized antibodies were also tested for their abilities to block the binding of human LAG3 to MHC II expressed on Daudi cells, according the protocol of Example 8. The data was shown in FIG. 5.

The abilities of the chimeric and humanized 101F4 and 134G10 antibodies to stimulate T cell response were determined by a MLR assay according to the protocol of Example 9 with some modifications. Briefly, PBMCs from one healthy human donor's blood sample were collected by density gradient centrifugation and re-suspended in RPMI1640 medium. PBMCs were cultured in a 37° C. incubator for 2 hours, and cells adhered to container walls were collected as isolated monocytes. The monocytes were cultured with 100 ng/ml recombinant human GM-CSF (R&D, US, Cat #: 7954-GM) and 100 ng/ml recombinant human IL-4 (R&D, US, Cat #: 6507-IL) in RPMI1640 medium supplemented with 10% FBS in a 24-well plate. Three days later, half of the medium was replaced with fresh medium. On day 6 of culturing, the culture medium was replaced by fresh medium containing 100 ng/ml recombinant human GM-CSF, 100 ng/ml recombinant human IL-4, 10 ng/ml rhTNF-α (R&D, US, Cat #: 210-TA-100), 1000 U/ml rhIL-6 (R&D, US, Cat #7270-IL-025), 1 μg/ml PGE2 (TOCRIS, US, Cat #363-24-6) and 10 ng/ml IL-1β (R&D, US, Cat #210-LB-025). The cells were cultured for another 2 days to generate DCs. Then, PBMCs from another healthy human donor's blood sample were collected by density gradient centrifugation and then re-suspended in RPMI1640 medium. CD4$^+$ T cells were isolated from the PBMCs using Invitrogen Dynabeads Untouched Human CD4+ T cells isolation kit (Thermal Fisher Scientific, USA, Cat #: 11346D) according to the manufacturer's instructions. The DCs from the first donor were seeded at 2.5×10$^4$ cells/well and the CD4$^+$ T cells from the second donor were seeded at 5×10$^4$ cells/well in 100 μl of complete medium (90% DMEM+10% FBS) in a 96 well U-bottom plate. An anti-human PD-1 antibody (nivolumab, also referred to as α-PD 1, prepared using the amino acid sequences disclosed in U.S. Pat. No. 8,008,449 with human IgG4/kappa constant regions, 100 μl per well, final concentration at 100 μg/ml) were added to the cells, and the plate was further cultured for five days. The cells were washed by PBS for 3 times, and then added with 100 μl of complete medium containing α-PD 1 (1 μg/ml), and 100 μl of complete medium containing anti-LAG3 antibodies (concentration at 100 μg/ml, 20 μg/ml or 4 μg/ml) or the control antibody Hel (LifeTein, US, Cat #: LT12031). The plate was further cultured for 72 h. IFN-γ concentration was determined by ELISA using an IFN-γ level determination kit (R&D, US, Cat #: SIF50) according to the manufacturer's protocol. The assay was done in triplicate. BMS was used as the positive control.

Figure 4:
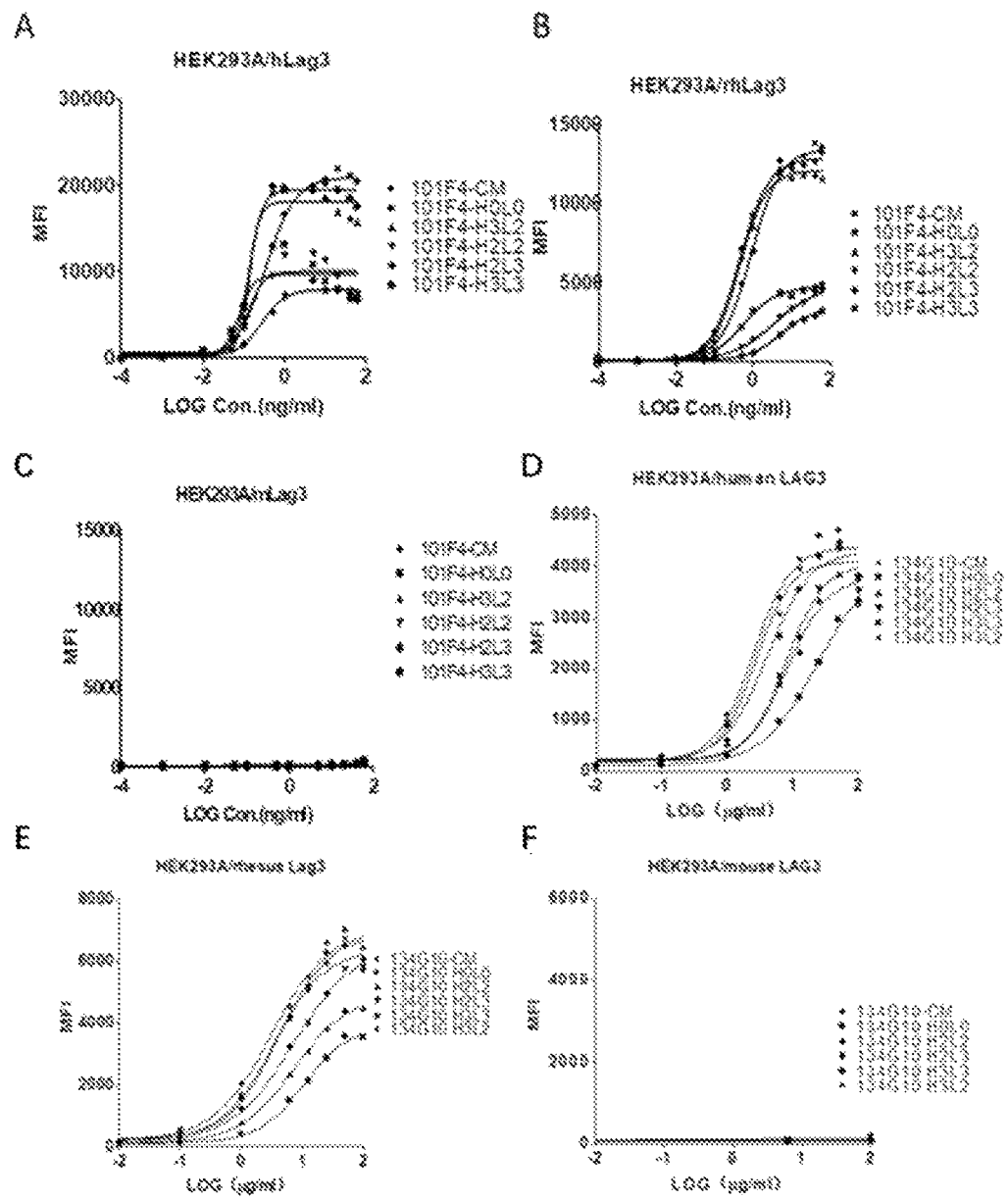
FIG. 4 shows the binding activities of chimeric and humanized 101F4 antibodies to HEK293A/human LAG3 (A), HEK293A/rhesus LAG3 (B), and HEK293A/mouse LAG3 (C), and the binding activities of chimeric and humanized 134G10 antibodies to HEK293A/human LAG3 (D), HEK293A/rhesus LAG3 (E), and HEK293A/mouse LAG3 (F).

As shown in FIG. 4, the humanized 134G10 antibodies had similar binding activies to their corresponding chimeric antibody, and binding activity differences were present among humanized 101F4 antibodies.

Figure 5:
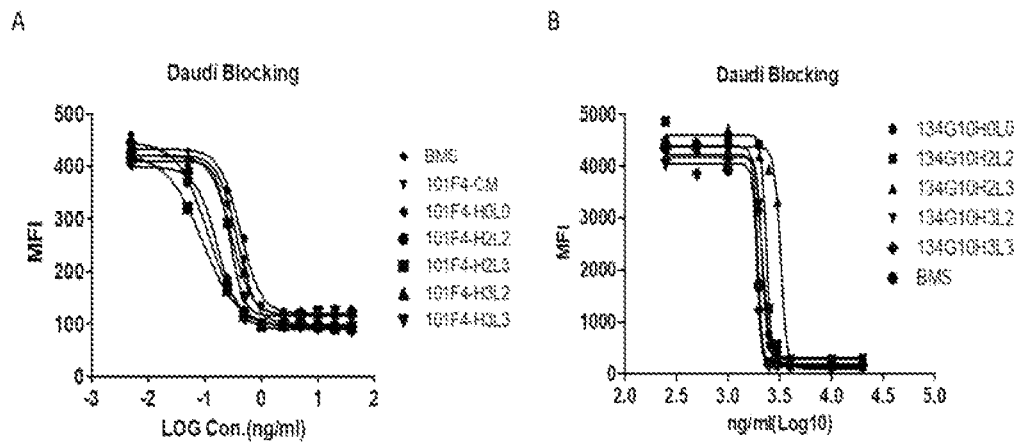
FIG. 5 shows the activities of humanized 101F4 (A) and 134G10 (B) antibodies on blocking LAG3 binding to MHCII on Daudi cells.

As shown in FIG. 5, all the humanized 101F4 and 134G10 antibodies had similar blocking capacities on LAG3 binding to MHC II to their respective chimeric antibody, which were comparable or better as compared to that of BMS.

Figure 6:
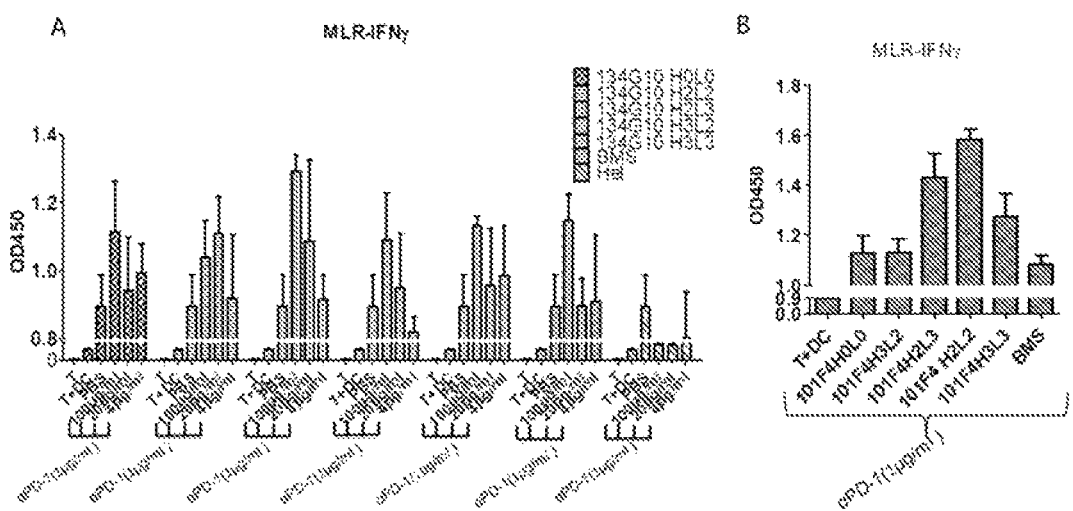
FIG. 6 shows humanized 134G10 (A) and 101F4 (B) antibodies, in combination with an anti-PD-1 antibody, induced T cell activation, as measured by IFN-γ secretion, in a dose dependent manner.

As shown in FIG. 6, all humanized 101F4 and 134G10 antibodies promoted αPD-1 pretreated T cell activation, with IFN-γ levels similar to or higher than that in the BMS group. Antibodies 101F4H2L2 and 134G10H2L3 showed the best promoting effect on T cell response.

Example 14 Affinity Maturation of Humanized Antibody 101F4H2L2 by Phage Display

To further improve the binding activity/affinity of the antibodies herein, 101F4H2L2 was selected for affinity maturation by phage display techniques. Briefly, three-dimensional structural modeling simulation was performed to identify potential residues in the heavy and light chain CDRs of 101F4H2L2 that might be important for binding activity/affinity. The CDR residues as identified were used for heavy/light chain mutagenesis by PCRs using specially designed primers and standard protocol for site-directed mutagenesis. A phage display library was then constructed and subjected to biopanning using hLAG3-hFc bound agarose beads. After three rounds of screening and enrichment, high binders were selected, harvested and then used to infect bacterial cells. Bacterial colonies were picked up and grown onto 96-well plates. Cell-based ELISA was performed to identify high binders which were sequenced later. The beneficial mutations in the heavy and light chain CDRs were identified and then used to construct a new phage display library, which was subjected to another 3 rounds of biopanning. The highest binder, 101F4H2L2-8, was identified, which contained three mutations at the VH CDR3 region and one mutation at the VL CDR3 region as compared to its parent clone 101F4H2L2. It was then expressed in HEK293F cells as a full length, IgG4(S228P)/kappa antibody.

The binding activities of 101F4H2L2 and 101F4H2L2-8 to human LAG3 were tested by ELISA according the protocol of Example 5. The binding activities of these two antibodies to HEK293 cells expressing human LAG3, rhLAG3 or mouse LAG3 were tested by FACS following the protocol described in Example 6. Further, the binding activities of the two antibodies to actived human PBMCs were investigated by FACS. Briefly, human PBMCs were collected by density gradient centrifugation and then re-suspended in the complete medium (RPMI medium+10% FBS+ human IL-2 (20 IU/ml, R&D, Cat #: 202-IL)+ Dynabeads™ Human T-Activator CD3/CD28 (Gibco, Cat #: 11132D)) at 37° C. under 5% CO$_2$ in a humidified incubator for 2 days to get activated T cells. The cells were then collected and tested by FACS as described in Example 6.

Figure 7:
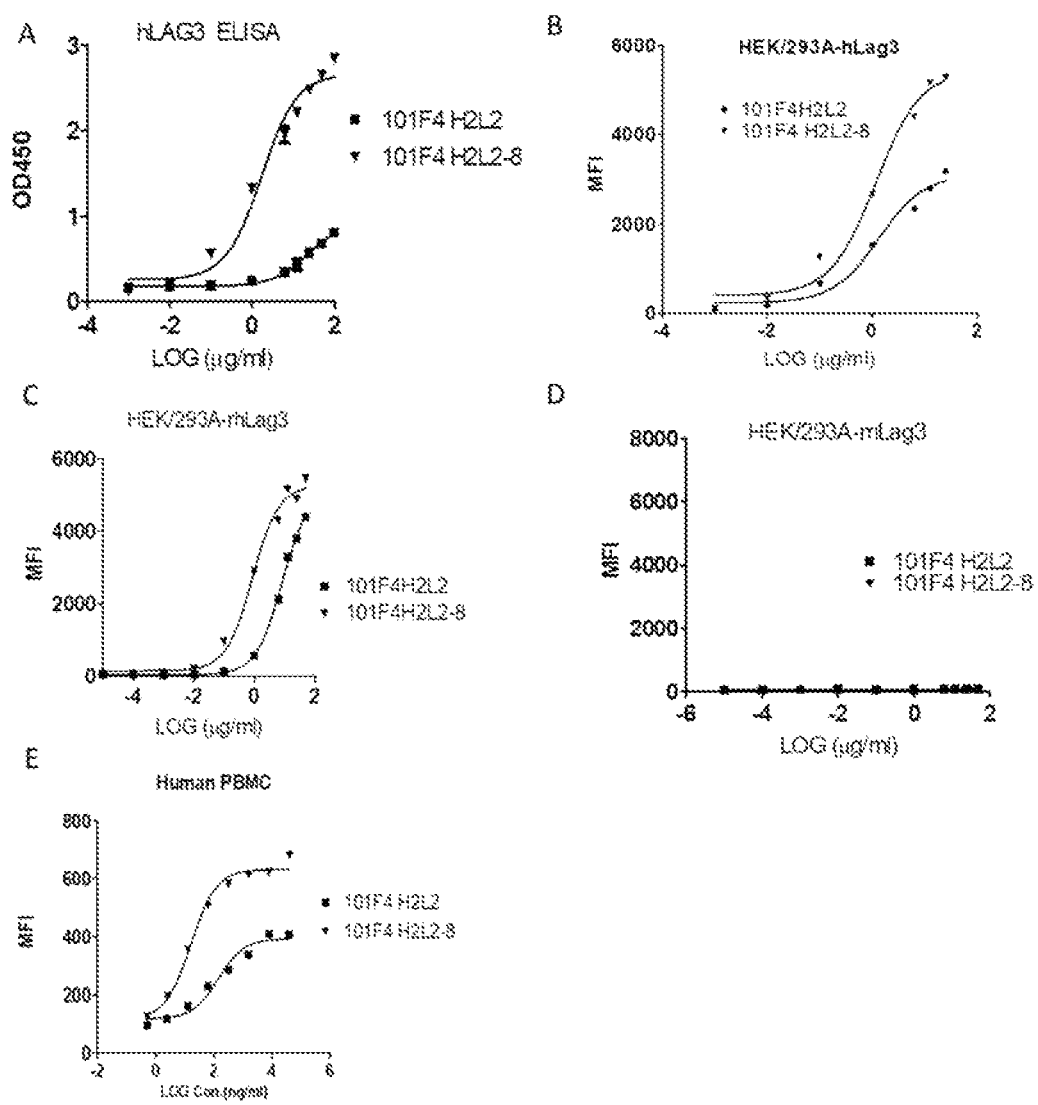
FIG. 7 shows the binding activities of humanized antibodies 101F4H2L2 and 101F4H2L2-8 to human LAG3 (A), HEK293A/human LAG3 (B), HEK293A/rhesus LAG3 (C), HEK293A/mouse LAG3 (D) and activated human PBMC (E).

The results were shown in FIG. 7, suggesting that 101F4H2L2-8 had significantly improved binding activities to free and cell surface expressed human and monkey LAG3 proteins, compared to 101F4H2L2.

Example 15 Binding Affinities of Exemplary Chimeric or Humanized Anti-LAG3 Antibodies to Human and Monkey LAG3 by SPR The chimeric and humanized antibodies were tested for binding affinities to human and monkey LAG3 proteins with the BIAcore™ 8K instrument (GE Life Sciences). Briefly, 100-200 response units (RU) of human LAG3(ECD)-his protein (Sino Biological, CN, Cat #: 16498-H02H) or monkey LAG3(ECD)-mFc protein (ACRO, CN, Cat #: LA3-052A0) were coupled to CM5 biosensor chips (Cat #: BR-1005-30, GE Life Sciences), and the un-reacted groups were blocked with 1M ethanolamine. Serially diluted antibodies at concentrations ranging from 0.3 μM to 10 μM were injected into the SPR running buffer (HBS-EP buffer, pH7.4, GE Life Sciences; US; Cat #: BR-1006-69) at 30 μL/minute. The binding capacities were calculated with the RUs of blank controls subtracted. The association rate (Ka) and dissociation rate (Kd) were calculated using the one-to-one Langmuir binding model (BIA Evaluation Software, GE Life Sciences). The equilibrium dissociation constant $K_D$ was calculated as the kd/ka ratio.

Figure 8:
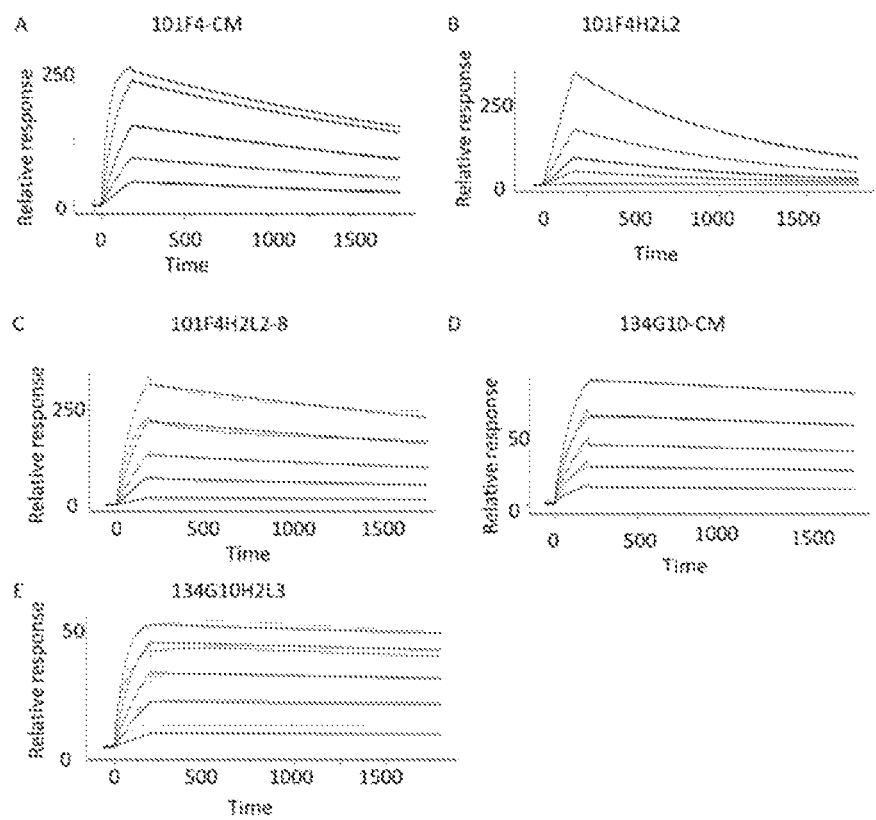
FIG. 8 shows the binding affinities of chimeric antibody 101F4-CM (A), humanized antibodies 101F4H2L2 (B) and 101F4H2L2-8 (C), chimeric antibody 134G10-CM (D), and humanized antibody 134G10H2L3 (E) to human LAG3.

The binding affinity curves of those chimeric or humanized antibodies to human LAG3 as measured by BIAcore™ were shown in FIG. 8, wherein the Ka values for 101F4-CM, 101F4H2L2, 101F4H2L2-8, 134G10-CM, and 134G10H2L3 were 4.03E+05, 9.60E+05, 1.04E+05, 9.39E+04 and 1.66E+05 respectively, the Ka values for these antibodies were 3.35E-04, 3.98E-01, 2.14E-04, 6.92E-05 and 4.35E-05, respectively, and the $K_D$ values for these antibodies were 8.33E-10, 4.14E-07, 2.05E-09, 7.37E-10 and 2.62E-10, respectively. The affinity matured antibody 101F4H2L2-8 had significantly higher binding affinity to human LAG3 as compared to its parent antibody 101F4H2L2.

Figure 9:
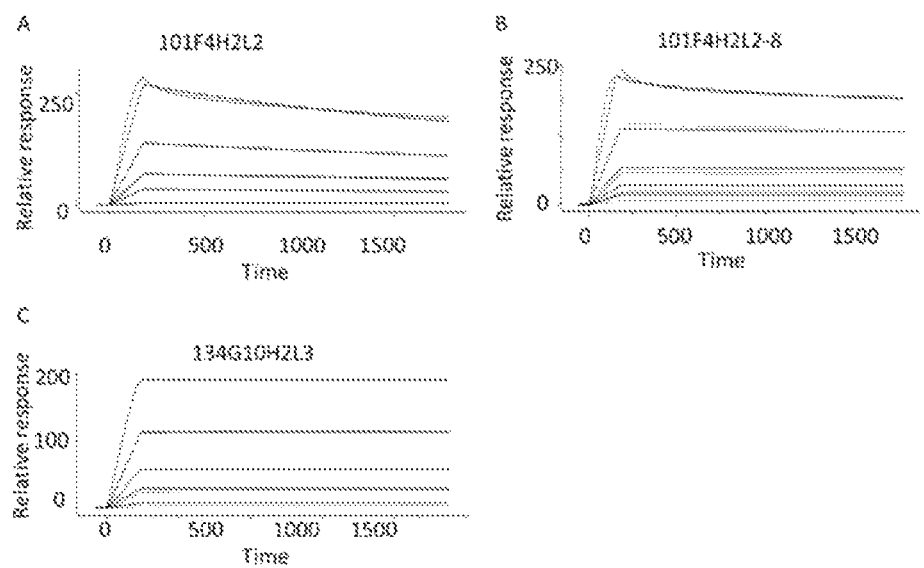
FIG. 9 shows the binding affinities of humanized antibodies 101F4H2L2 (A), 101F4H2L2-8 (B) and 134G10H2L3 (C) to monkey LAG3.

The binding affinity curves of antibodies 101F4H2L2, 101F4H2L2-8 and 134G10H2L3 to monkey LAG3 as measured by BIAcore™ were shown in FIG. 9, wherein the Ka values for 101F4H2L2, 101F4H2L2-8 and 134G10H2L3 were 3.94E+06, 1.62E+05 and 1.23E+07, respectively, the $K_d$ values for 101F4H2L2, 101F4H2L2-8 and 134G10H2L3 were 1.92E-03, 1.59E-04 and 2.46E-06, respectively, and the $K_D$ values for 101F4H2L2, 101F4H2L2-8 and 134G10H2L3 were 4.88E-10, 9.80E-10 and 2.01E-13, respectively. The data indicated that the binding affinity of 101F4H2L2-8 to monkey LAG3 was comparable to that to human LAG3, while the binding affinity of 134G10H2L3 to monkey LAG3 was higher than that to human LAG3.

Example 16 Affinity Maturated Antibodies Promoted T Cell Activation

The abilities of humanized antibodies 101F4H2L2 and 101F4H2L2-8 (with affinity maturation) to stimulate T cell response were determined by a MLR assay according to the protocol of Example 13. BMS was used as the positive control.

Based on the affinity maturation data in Example 14, 101F4H2L3-8, having three amino acid mutations at the VH CDR3 region and one amino acid mutation at the VL CDR3 region as mentioned above relative to 101F4H2L3, and 101F4H3L3-8, having three amino acid mutations at the VH CDR3 region and one amino acid mutation at the VL CDR3 region as mentioned above relative to 101F4H3L3, were constructed. 101F4H2L3-8 and 101F4H3L3-8 were prepared as full length, IgG4 (S228P)/kappa antibodies as described in Example 10, purified as described in Example 4, and tested for their abilities on T cell activation promotion as described in Example 13. BMS was used as the positive control.

Figure 10:
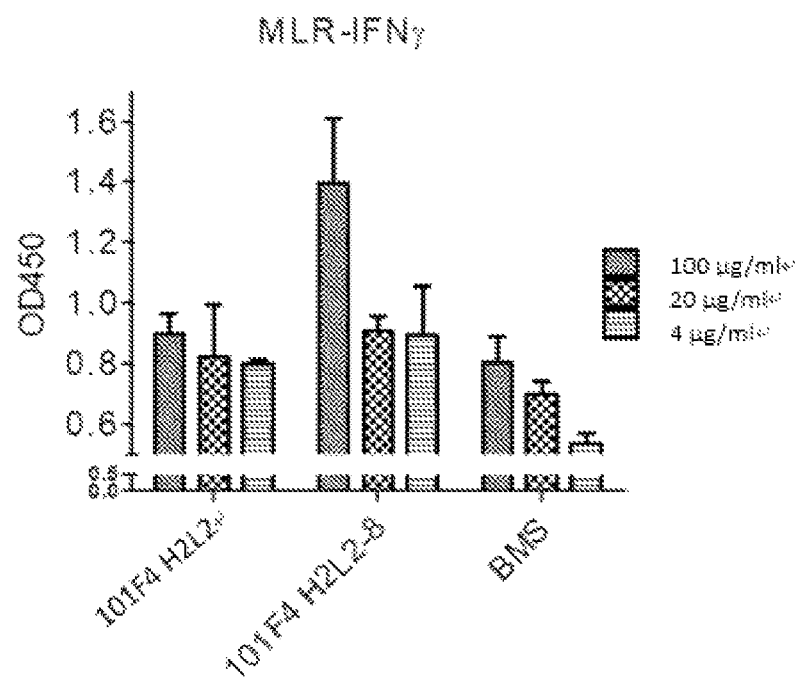
FIG. 10 shows the humanized antibodies 101F4H2L2 and 101F4H2L2-8 (A), 101F4H2L3-8 and 101F4H3L3-8 (B), in combination with an anti-PD-1 antibody, promoted T cell activation.
Figure 10:
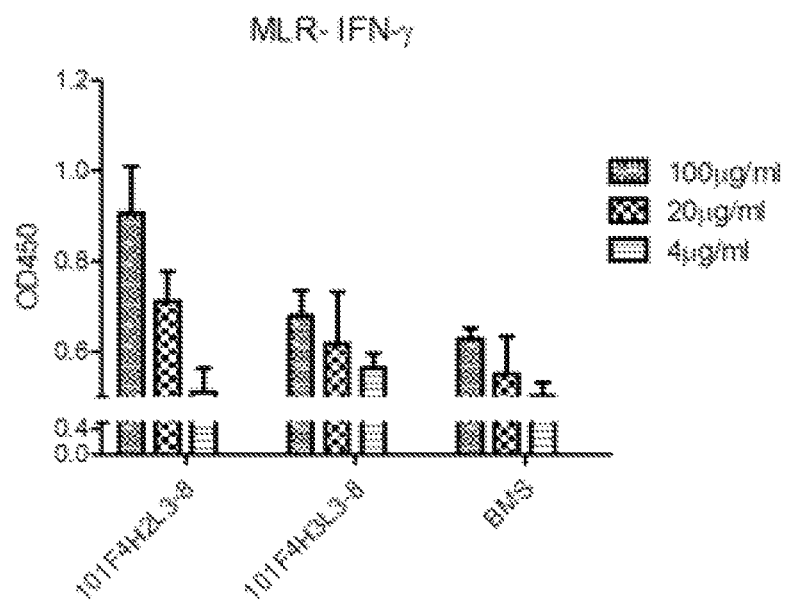

As shown in FIG. 10, all the humanized antibodies with or without affinity maturation promoted activation of anti-PD-1 pretreated T cells, and antibodies 101F4H2L2, 101F4H2L2-8, 101F4H2L3-8 and 101F4H3L3-8 showed comparable or higher promoting capacities as compared to BMS. 101F4H2L2-8 showed the highest promoting activity, wherein it induced more IFN-γ secretion than 101F4H2L2, especially when at the high concentration.

Example 17 Humanized Antibodies had In Vivo Anti-Tumor Effect

In vivo anti-tumor activities of anti-LAG3 antibodies 101F4H2L2, 101F4H2L2-8 and 134G10H2L3, each having human IgG4 (S228P)/kappa constant regions, were studied in an animal model established by grafting MC38 murine colon adenocarcinoma in transgenic mice with human LAG3 (GemPharmatech Co. Ltd, China). An anti-LAG3 antibody MK-4280 (prepared using the amino acid sequences disclosed in WO 2016/028672A1 with human IgG4 (S228P)/kappa constant regions) was used as the positive control.

Mice were subcutaneously injected with $1 \times 10^6$ MC38 cells at one flank and randomly assigned into 5 groups, 10 mice per group, on Day 0. These animals were then i.p. administered with 101F4H2L2 (10 mg/kg), 101F4H2L2-8 (10 mg/kg), 134G10H2L3 (10 mg/kg), MK-4280 (10 mg/kg), and PBS, respectively, on Day 0, 4, 7, 11, 14 and 18.

The in vivo anti-tumor effects of 101F4H2L2-8 and 134G10H2L3 were further tested in human PD-1×LAG3-double knock in mice (GemPharmatech Co. Ltd, China). BMS-986016 with human IgG4 (S228P)/kappa constant regions was used as the positive control. Briefly, mice were subcutaneously injected with $1 \times 10^6$ MC38 cells at one flank and randomly assigned into 4 groups, 10 mice per group, on Day 0. These animals were then i.p. administered with 101F4H2L2-8 (10 mg/kg), 134G10H2L3 (10 mg/kg), BMS (10 mg/kg), and PBS, respectively, on Day 0, 4, 7, 11, 14 and 18.

Tumor size and mice body weight were measured over time. Tumor measurements (width and length) were taken by caliper and tumor volume was calculated by the formula TV=(length×width$^2$)/2. The tumor volume changes were shown in FIG. 11 and FIG. 12, and tumor volume differences among groups were analyzed by one-way ANOVA.

On Day 25, the mice were sacrificed. The tumors were isolated and weighed, and placed in Hanks buffer with collagenases. The tumors were then cut into small pieces and incubated in Hanks buffer with collagenases at 37° C. for 30 min with gentle shaking. Thereafter, 10 ml of RPMI 1640+10% FBS was added to each sample to deactivate the collagenase and maintain viability of the immune cells. Samples were passed through a 70 μm cell filter membrane (Corning, Cat #: 352350) and placed in new tubes. The samples were pelleted and re-suspended in PBSF buffer (PBS+2% FBS) at a density of $1 \ast 10^7$ cells/ml. The samples were washed by PBSF buffer for twice, and added with 1 μg/ml anti-CD45 (Brilliant Violet 785™ anti-mouse CD45 Antibody; Biolegend; US; Cat #: 103149), 1 μg/ml anti-CD8 (APC anti-mouse CD8a Antibody; Biolegend; US; Cat #: 100712) and 1 μg/ml anti-CD3 (FITC anti-mouse CD3 Antibody; Biolegend; US; Cat #: 100203). The resultant mixtures were incubated for half an hour at 4° C. Cells were washed twice by PBSF buffer and analyzed on a FACS machine (BD).

Figure 11:
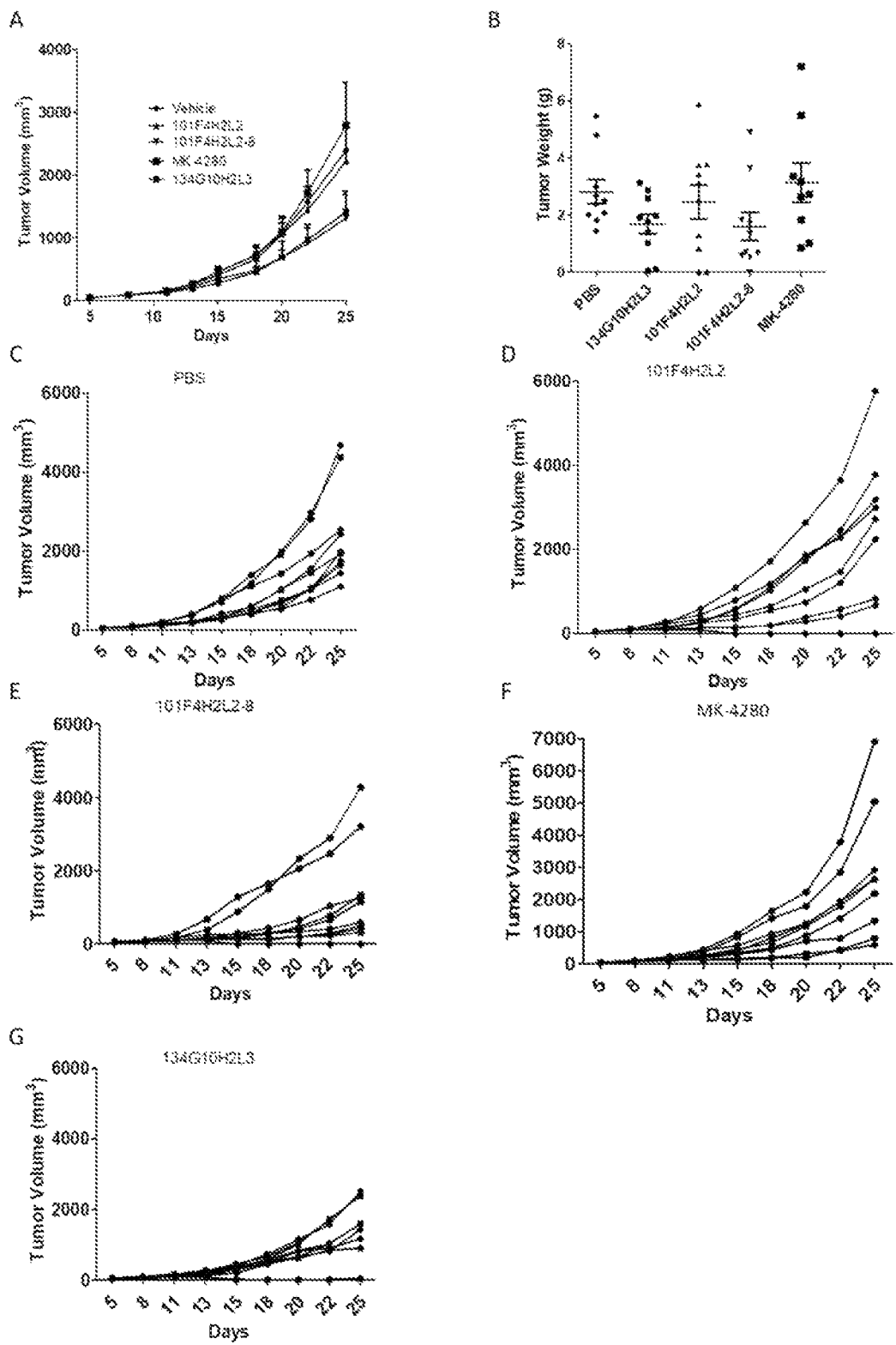
FIG. 11 shows average tumor volume changes (A) and average tumor weight on Day 25 (B) in transgenic mice with human LAG3 from groups treated with vehicle (PBS), humanized antibodies 101F4H2L2, 101F4H2L2-8, 134G10H2L3, or positive control, and tumor volume changes in individual mice from groups treated with vehicle (C), 101F4H2L2 (D), 101F4H2L2-8 (E), positive control (F) and 134G10H2L3 (G).
Figure 12:
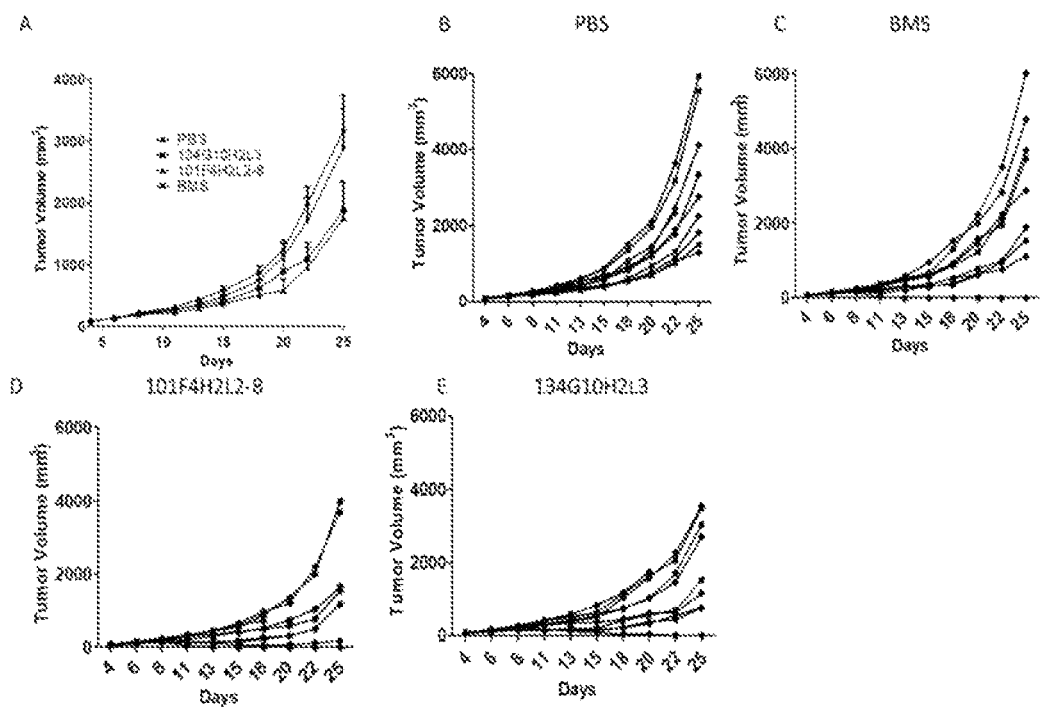
FIG. 12 shows average tumor volume changes (A) in transgenic mice with human LAG3 and PD-1 from groups treated with vehicle, humanized antibodies 134G10H2L3, 101F4H2L2-8 or positive control, and tumor volume changes in individual mice from groups treated with vehicle (B), positive control (C), 101F4H2L2-8 (D) and 134G10H2L3 (E).

As shown in FIG. 11 and FIG. 12, antibodies 101F4H2L2-8 and 134G10H2L3 significantly inhibited tumor growth in transgenic mice with human LAG3, with the best anti-tumor effects among tested antibodies.

Figure 13:
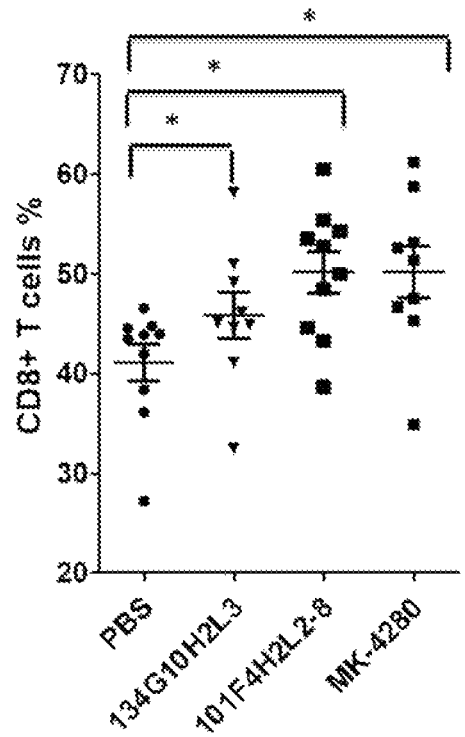
FIG. 13 shows the in vivo effect of anti-LAG3 antibodies on proliferation of CD45+CD3+CD8+ T cell in peripheral blood from transgenic mice with human LAG3.

As shown in FIG. 13, the antibodies 101F4H2L2-8 and 134G10H2L3 significantly increased tumor infiltrating CD8$^+$ T cells in transgenic mice with human LAG3.

Example 18 Humanized Antibodies Enhanced In Vivo Anti-Tumor Activity of Anti-PD1 Antibody The synergistic in vivo anti-tumor effect of antibody 101F4H2L2-8 or 134G10H2L3, with an anti-PD-1 antibody (InVivoMAb anti-mouse PD-1(CD279), Cat #BE0146, USA), was studied, using an animal model established by grafting MC38 murine colon adenocarcinoma in transgenic mice with human LAG3 (GemPharmatech Co. Ltd, China). Mice were subcutaneously injected with $1 \times 10^6$ MC38 cells at one flank and randomly assigned into 8 groups, 10 mice per group, on Day 0. Four groups of animals were i.p. administered with 101F4H2L2-8 (10 mg/kg), anti-PD-1 antibody (1 mg/kg), 101F4H2L2-8+ anti-PD-1 (10 mg/kg+1 mg/kg), and PBS, respectively, on Day 0, 4, 7, 11, 14, and 18. The remaining four groups of animals were i.p. administered with 134G10H2L3 (10 mg/kg), anti-PD-1 antibody (2.5 mg/kg), 134G10H2L3+ anti-PD-1 (10 mg/kg+2.5 mg/kg), and PBS, respectively, on Day 0, 4, 7, 11, 14, and 18.

Tumor size and mice body weight were monitored over time. Tumor measurements (width and length) were taken by caliper and tumor volume was calculated by the formula TV=(length×width$^2$)/2. The experiment was terminated before the tumor volume in antibody administration groups reached 3.5 cm$^3$. Tumor volume differences among groups were analyzed by one-way ANOVA.

Figure 14:
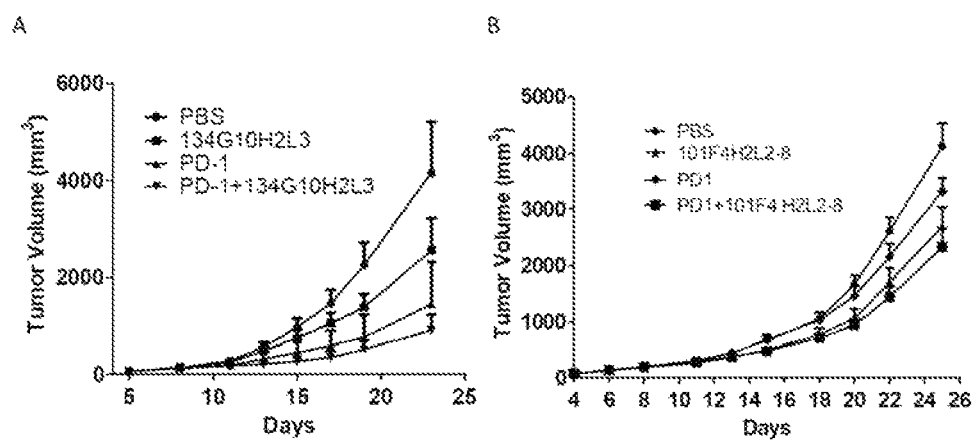
FIG. 14 shows average tumor volume changes (A) in groups treated with vehicle (PBS), humanized antibody 134G10H2L3, an anti-PD-1 antibody, or 134G10H2L3 in combination with an anti-PD-1 antibody, and average tumor volume changes (B) in groups treated with vehicle (PBS), humanized antibody 101F4H2L2-8, an anti-PD-1 antibody, or 101F4H2L2-8 in combination with an anti-PD-1 antibody.

The results were shown in FIG. 14. According to the data, although individual differences were observed in mice of each group, 101F4H2L2-8 and 134G10H2L3 evidently inhibited tumor growth as compared to the vehicle groups. When the anti-LAG3 antibodies were used in combination with the anti-PD-1 antibodies, the anti-tumor effect was better than single antibody therapies.

Amino acid sequences of some exemplary antibodies' heavy/light chain variable regions were summarized in table 6.

TABLE 6

Sequences

Description/
Sequence/SEQ ID NO.

VH-CDR1 of mouse, chimeric and humanized (with or without affinity maturation) 101F4 antibodies
DYEMH (SEQ ID NO: 1)

VH-CDR2 of mouse, chimeric and humanized (with or without affinity maturation) 101F4 antibodies
AIDPETGGIVYNQRFKG (SEQ ID NO: 2)

VH-CDR3 of mouse, chimeric and humanized (without affinity maturation) 101F4 antibodies
AGWGY (SEQ ID NO: 3)

VH-CDR3 of humanized (with affinity maturation) 101F4 antibodies
TGWND (SEQ ID NO: 4)

VL-CDR1 of mouse, chimeric and humanized (with or without affinity maturation) 101F4 antibodies
KASQDINSYLS (SEQ ID NO: 5)

VL-CDR2 of mouse, chimeric and humanized (with or without affinity maturation) 101F4 antibodies
RANRLLD (SEQ ID NO: 6)

VL-CDR3 of mouse, chimeric and humanized (without affinity maturation) 101F4 antibodies
LQYDEFPFT (SEQ ID NO: 7)

VL-CDR3 of humanized (with affinity maturation) 101F4 antibodies
QQYDEFPFT (SEQ ID NO: 8)

VH of mouse and chimeric 101F4 antibodies
EVQLEQSGAELVRPGASVTLSCKASGYTFT<u>DYEMH</u>WVKQTPVYGLEWMG<u>AIDPETGGI
VYNQRFKG</u>KAILTADKSSSTAYMELRSLTSEDSAVYYCT<u>GAGWGY</u>WGQGTTLTVSS
(SEQ ID NO: 9)

VH of humanized antibody 101F4H0L0
QVQLVQSGAEVKKPGASVKVSCKVSGYTFT<u>DYEMH</u>WVRQAPGKGLEWMG<u>AIDPETG
GIVYNQRFKG</u>RVTMTEDTSTDTAYMELSSLRSEDTAVYYCAT<u>AGWGY</u>WGQGTTVTVSS
(SEQ ID NO: 10)

VH of humanized antibodies 101F4H2L2 and 101F4H2L3
QVQLVQSGAEVKKPGASVKVSCKVSGYTFT<u>DYEMH</u>WVRQAPGKGLEWMG<u>AIDPETG
GIVYNQRFKG</u>RVTLTADTSTDTAYMELSSLRSEDTAVYYCAT<u>AGWGY</u>WGQGTTVTVS
S (SEQ ID NO: 11)

VH of humanized antibodies 101F4H3L2 and 101F4H3L3
QVQLVQSGAEVKKPGASVKVSCKASGYTFT<u>DYEMH</u>WVRQAPGKGLEWMG<u>AIDPETG
GIVYNQRFKG</u>RATLTADTSTDTAYMELSSLRSEDTAVYYCAG<u>AGWGY</u>WGQGTTVTVS
S (SEQ ID NO: 12)

VH of humanized (with affinity maturation) antibodies 101F4H2L2-8 and 101F4H2L3-8
QVQLVQSGAEVKKPGASVKVSCKVSGYTFT<u>DYEMH</u>WVRQAPGKGLEWMG<u>AIDPETG
GIVYNQRFKG</u>RVTLTADTSTDTAYMELSSLRSEDTAVYYCAT<u>TGWND</u>WGQGTTVTVSS
(SEQ ID NO: 13)

VH of humanized (with affinity maturation) antibody 101F4H3L3-8
QVQLVQSGAEVKKPGASVKVSCKASGYTFT<u>DYEMH</u>WVRQAPGKGLEWMG<u>AIDPETG
GIVYNQRFKG</u>RATLTADTSTDTAYMELSSLRSEDTAVYYCAG<u>TGWND</u>WGQGTTVTVS
S (SEQ ID NO: 14)

TABLE 6-continued

Sequences

Description/
Sequence/SEQ ID NO.

VL of mouse and chimeric 101F4 antibodies
DIVITQSPSSMYASLGERVTITC<u>KASQDINSYLS</u>WFQQKPGKSPKTLIY<u>RANRLLDGVPSR</u>
FSGSGSGQDYSLTISSLEFEDMGLYYC<u>LQYDEFPFT</u>FGSGTKLEIK (SEQ ID NO: 15)

VL of humanized antibody 101F4H0L0
DIQMTQSPSSLSASVGDRVTITC<u>KASQDINSYLS</u>WYQQKPGKAPKLLIY<u>RANRLLDGVPS</u>
RFSGSGSGTDFTLTISSLQPEDFATYYC<u>LQYDEFPFT</u>FGQGTKLEIK (SEQ ID NO: 16)

VL of humanized antibodies 101F4H2L2 and 101F4H3L2
DIQMTQSPSSLSASVGDRVTITC<u>KASQDINSYLS</u>WYQQKPGKAPKLLIY<u>RANRLLDGVPS</u>
RFSGSGSGQDYTLTISSLQPEDFATYYC<u>LQYDEFPFT</u>FGQGTKLEIK (SEQ ID NO: 17)

VL of humanized (with affinity maturation) antibody 101F4H2L2-8
DIQMTQSPSSLSASVGDRVTITC<u>KASQDINSYLS</u>WYQQKPGKAPKLLIY<u>RANRLLDGVPS</u>
RFSGSGSGQDYTLTISSLQPEDFATYYC<u>QQYDEFPFT</u>FGQGTKLEIK (SEQ ID NO: 18)

VL of humanized antibodies 101F4H2L3 and 101F4H3L3
DIQITQSPSSLSASVGDRVTITC<u>KASQDINSYLS</u>WFQQKPGKAPKLLIY<u>RANRLLDGVPSR</u>
FSGSGSGQDYTLTISSLQPEDFATYYC<u>LQYDEFPFT</u>FGQGTKLEIK (SEQ ID NO: 19)

VL of humanized (with affinity maturation) antibodies 101F4H2L3-8 and 101F4H3L3-8
DIQITQSPSSLSASVGDRVTITC<u>KASQDINSYLS</u>WFQQKPGKAPKLLIY<u>RANRLLDGVPSR</u>
FSGSGSGQDYTLTISSLQPEDFATYYC<u>QQYDEFPFT</u>FGQGTKLEIK (SEQ ID NO: 20)

VH-CDR1 of mouse, chimeric and humanized 134G10 antibodies
SFGMS (SEQ ID NO: 21)

VH-CDR2 of mouse, chimeric and humanized 134G10 antibodies
IISSGGTYTFYPDILKG (SEQ ID NO: 22)

VH-CDR3 of mouse, chimeric and humanized 134G10 antibodies
VYSDYDGRFDY (SEQ ID NO: 23)

VL-CDR1 of mouse, chimeric and humanized 134G10 antibodies
KSSQSLLNSGNQKNYLA (SEQ ID NO: 24)

VL-CDR2 of mouse, chimeric and humanized 134G10 antibodies
GASTRES (SEQ ID NO: 25)

VL-CDR3 of mouse, chimeric and humanized 134G10 antibodies
QNDHSYPLT (SEQ ID NO: 26)

VH of mouse and chimeric 134G10 antibodies
EVQLVESGGDLVKPGGSLKLSCAASGFTFS<u>SFGMS</u>WVRQTPDKRLEWVG<u>IISSGGTYTF
YPDILKG</u>RFTISRDNAKNTLYLQMSSLKSEDTAMYYCAR<u>VYSDYDGRFDY</u>WGQGTTLT
VSS (SEQ ID NO: 27)

VH of humanized antibody 134G10H0L0
EVQLVESGGGLVKPGGSLRLSCAASGFTFS<u>SFGMS</u>WVRQAPGKGLEWVS<u>IISSGGTYTFY
PDILKG</u>RFTISRDNAKNSLYLQMNSLRAEDTAVYYCAR<u>VYSDYDGRFDY</u>WGQGTLVTVS
S (SEQ ID NO: 28)

VH of humanized antibodies 134G10H2L2 and 134G10H2L3
EVQLVESGGGLVKPGGSLRLSCAASGFTFS<u>SFGMS</u>WVRQAPGKRLEWVS<u>IISSGGTYTF
YPDILKG</u>RFTISRDNAKNSLYLQMNSLRAEDTAVYYCAR<u>VYSDYDGRFDY</u>WGQGTLVT
VSS (SEQ ID NO: 29)

VH of humanized antibodies 134G10H3VL2 and 134G10H3L3
EVQLVESGGGLVKPGGSLRLSCAASGFTFS<u>SFGMS</u>WVRQAPGKRLEWVG<u>IISSGGTYTF
YPDILKG</u>RFTISRDNAKNSLYLQMNSLRAEDTAVYYCAR<u>VYSDYDGRFDY</u>WGQGTLVT
VSS (SEQ ID NO: 30)

VL of mouse and chimeric 134G10 antibodies
DIVMTQSPSSLSVSAGEKVTMNC<u>KSSQSLLNSGNQKNYLA</u>WYQQKPGQPPKLLIY<u>GAST
RES</u>GVPDRFTGSGSGTDFTLTISSVQAEDLAVYYC<u>QNDHSYPLT</u>FGAGTKLELK (SEQ
ID NO: 31)

VL of humanized antibody 134G10H0L0
DIVMTQSPDSLAVSLGERATINC<u>KSSQSLLNSGNQKNYLA</u>WYQQKPGQPPKLLIY<u>GAST
RES</u>GVPDRFSGSGSGTDFTLTISSLQAEDVAVYYC<u>QNDHSYPLT</u>FGQGTKLEIK (SEQ ID
NO: 32)

TABLE 6-continued

Sequences

Description/
Sequence/SEQ ID NO.

VL of humanized antibodies 134G10H2L2 and 134G10H3L2
DIVMTQSPSSLAVSLGERATINC<u>KSSQSLLNSGNQKNYLA</u>WYQQKPGQPPKLLIY<u>GAST
RES</u>GVPDRFSGSGSGTDFTLTISSLQAEDVAVYYC<u>QNDHSYPLT</u>FGAGTKLEIK (SEQ ID
NO: 33)

VL of humanized antibodies 134G10H2L3 and 134G10H3L3
DIVMTQSPSSLAVSLGERATINC<u>KSSQSLLNSGNQKNYLA</u>WYQQKPGQPPKLLIY<u>GAST
RES</u>GVPDRFTGSGSGTDFTLTISSLQAEDVAVYYC<u>QNDHSYPLT</u>FGAGTKLEIK (SEQ ID
NO: 34)

Human IgG4 heavy chain constant region with S228P mutation
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLGK (SEQ ID NO: 35)

Human kappa light chain constant region
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC (SEQ ID NO: 36)

Human LAG3
ATGTGGGAGGCCCAGTTCCTGGGCCTGCTGTTCCTGCAGCCCCTGTGGGTGGCCCCC
GTGAAGCCCCTGCAGCCCGGCGCCGAGGTGCCCGTGGTGTGGGCCCAGGAGGGCGC
CCCCGCCCAGCTGCCCTGCAGCCCCACCATCCCCCTGCAGGACCTGAGCCTGCTGCG
CCGCGCCGGCGTGACCTGGCAGCACCAGCCCGACAGCGGCCCCCCGCCGCCGACCC
CCGGCCACCCCCTGGCCCCGGCCCCACCCGCCGCCCCCAGCAGCTGGGGCCCCC
GCCCCCGCCGCTACACCGTGCTGAGCGTGGGCCCCGGCGGCCTGCGCAGCGGCCGC
CTGCCCCTGCAGCCCCGCGTGCAGCTGGACGAGCGCGGCCGCCAGCGCGGCGACTT
CAGCCTGTGGCTGCGCCCCGCCCGCCGCGCCGACGCCGGCGAGTACCGCGCCGCCG
TGCACCTGCGCGACCGCGCCCTGAGCTGCCGCCTGCGCCTGCGCCTGGGCCAGGCCA
GCATGACCGCCAGCCCCCCGGCAGCCTGCGCGCCAGCGACTGGGTGATCCTGAAC
TGCAGCTTCAGCCGCCCCGACCGCCCCGCCAGCGTGCACTGGTTCCGCAACCGCGGC
CAGGGCCGCGTGCCCGTGCGCGAGAGCCCCCACCACCACCTGGCCGAGAGCTTCCT
GTTCCTGCCCCAGGTGAGCCCCATGGACAGCGGCCCCTGGGGCTGCATCCTGACCTA
CCGCGACGGCTTCAACGTGAGCATCATGTACAACCTGACCGTGCTGGGCCTGGAGC
CCCCCACCCCCCTGACCGTGTACGCCGGCGCCGGCAGCCGCGTGGGCCTGCCCTGCC
GCCTGCCCGCCGGCGTGGGCACCCGCAGCTTCCTGACCGCCAAGTGGACCCCCCCG
GCGGCGGCCCCGACCTGCTGGTGACCGGCGACAACGGCGACTTCACCCCTGCGCCTG
GAGGACGTGAGCCAGGCCCAGGCCGGCACCTACACCTGCCACATCCACCTGCAGGA
GCAGCAGCTGAACGCCACCGTGACCCTGGCCATCATCACCGTGACCCCCAAGAGCT
TCGGCAGCCCCGGCAGCCTGGGCAAGCTGCTGTGCGAGGTGACCCCCGTGAGCGGC
CAGGAGCGCTTCGTGTGGAGCAGCCTGGACACCCCCAGCCAGCGCAGCTTCAGCGG
CCCCTGGCTGGAGGCCCAGGAGGCCCAGCTGCTGAGCCAGCCCTGGCAGTGCCAGC
TGTACCAGGGCGAGCGCCTGCTGGGCGCCGCCGTGTACTTCACCGAGCTGAGCAGC
CCCGGCGCCCAGCGCAGCGGCCGCGCCCCCGGCGCCCTGCCCGCCGGCCACCTGCT
GCTGTTCCTGATCCTGGGCGTGCTGAGCCTGCTGCTGCTGGTGACCGGCGCCTTCGG
CTTCCACCTGTGGCGCCGCCAGTGGCGCCCCCGCCGCTTCAGCGCCCTGGAGCAGGG
CATCCACCCCCCCAGGCCCAGAGCAAGATCGAGGAGCTGGAGCAGGAGCCCGAGC
CCGAGCCCGAGCCCGAGCCCGAGCCCGAGCCCGAGCCCGAGCCCGAGCAGCTGTAA
(SEQ ID NO: 37)

Monkey LAG3
ATGTGGGAGGCCCAGTTCCTGGGCCTGCTGTTCCTGCAGCCCCTGTGGGTGGCCCCC
GTGAAGCCCCCCAGCCCGGCGCCGAGATCAGCGTGGTGTGGGCCCAGGAGGGCGC
CCCCGCCCAGCTGCCCTGCAGCCCCACCATCCCCCTGCAGGACCTGAGCCTGCTGCG
CCGCGCCGGCGTGACCTGGCAGCACCAGCCCGACAGCGGCCCCCCGCCCCCGCCC
CCGGCCACCCCCCGCCCCGGCCACCGCCCCGCCGCCCCTACAGCTGGGGCCCCC
GCCCCCGCCGCTACACCGTGCTGAGCGTGGGCCCCGGCGGCCTGCGCAGCGGCCGC
CTGCCCCTGCAGCCCCGCGTGCAGCTGGACGAGCGCGGCCGCCAGCGCGGCGACTT
CAGCCTGTGGCTGCGCCCCGCCCGCCGCGCCGACGCCGGCGAGTACCGCGCCACCG
TGCACCTGCGCGACCGCGCCCTGAGCTGCCGCCTGCGCCTGCGCGTGGGCCAGGCC
AGCATGACCGCCAGCCCCCCGGCAGCCTGCGCACCAGCGACTGGGTGATCCTGAA
CTGCAGCTTCAGCCGCCCCGACCGCCCCGCCAGCGTGCACTGGTTCCGCAGCCGCGG
CCAGGGCCGCGTGCCCGTGCAGGGCAGCCCCACCACCACCTGGCCGAGAGCTTCC
TGTTCCTGCCCACGTGGGCCCATGGACAGCGGCCTGTGGGGCTGCATCCTGACCT
ACCGCGACGGCTTCAACGTGAGCATCATGTACAACCTGACCGTGCTGGGCCTGGAG
CCCCCACCCCCCTGACCGTGTACGCCGGCGCCGGCAGCCGCGTGGGAGCTGCCCTGC
CGCCTGCCCCCCGCCGTGGGCACCCAGAGCTTCCTGACCGCCAAGTGGGCCCCCCC
GGCGGCGGCCCCGACCTGCTGGTGGCCGGCGACAACGGCGACTTCACCCTGCGCCT
GGAGGACGTGAGCCAGGCCCAGGCCGGCACCTACATCTGCCACATCCGCCTGCAGG
GCCAGCAGCTGAACGCCACCGTGACCCTGGCCATCATCACCGTGACCCCCAAGAGC
TTCGGCAGCCCCGGCAGCCTGGGCAAGCTGCTGTGCGAGGTGACCCCCGCCAGCGG TABLE 6-continued Sequences Description/
Sequence/SEQ ID NO.

CCAGGAGCACTTCGTGTGGAGCCCCCTGAACACCCCCAGCCAGCGCAGCTTCAGCG
GCCCCTGGCTGGAGGCCCAGGAGGCCCAGCTGCTGAGCCAGCCCTGGCAGTGCCAG
CTGCACCAGGGCGAGACCCTGCTGGGCGCCGCCGTGTACTTCACCGAGCTGAGCAG
CCCCGGCGCCCAGCGCAGCGGCCGCGCCCCGGCGCCCTGCGCGCCGGCCACCTGC
CCCTGTTCCTGATCCTGGGCGTGCTGTTCCTGCTGCTGCTGGTGACCGGCGCCTTCGG
CTTCCACCTGTGGCGCCGCCAGTGGCGCCCCGCCGCTTCAGCGCCCTGGAGCAGGG
CATCCACCCCCCCAGGCCCAGAGCAAGATCGAGGAGCTGGAGCAGGAGCCCGAGC
TGGAGCCCGAGCCCGAGCTGGAGCGCGAGCTGGCCCCGAGCCCGAGCCCGGCCCC
GAGCCCGAGCCCGAGCAGCTGTAA (SEQ ID NO: 38)

Mouse LAG3
ATGCGCGAGGACCTGCTGCTGGGCTTCCTGCTGCTGGGCCTGCTGTGGGAGGCCCCC
GTGGTGAGCAGCGGCCCCGGCAAGGAGCTGCCCGTGGTGTGGGCCCAGGAGGGCGC
CCCCGTGCACCTGCCCTGCAGCCTGAAGAGCCCCAACCTGGACCCCAACTTCCTGCG
CCGCGGCGGCGTGATCTGGCAGCACCAGCCCGACAGCGGCCAGCCCACCCCCATCC
CCGCCCTGGACCTGCACCAGGGCATGCCCAGCCCCCGCCAGCCCGCCCCCGGCCGCT
ACACCGTGCTGAGCGTGGCCCCCGGCGGCCTGCGCAGCGGCCGCCAGCCCCTGCAC
CCCCACGTGCAGCTGGAGGAGCGCGGCCTGCAGCGCGGCGACTTCAGCCTGTGGCT
GCGCCCCGCCCTGCGCACCGACGCCGGCGAGTACCACGCCACCGTGCGCCTGCCCA
ACCGCGCCCTGAGCTGCAGCCTGCCCTGCGCGTGGGCCAGGCCAGCATGATCGCC
AGCCCCAGCGGCGTGCTGAAGCTGAGCGACTGGGTGCTGCTGAACTGCAGCTTCAG
CCGCCCCGACCGCCCCGTGAGCGTGCACTGGTTCCAGGGCCAGAACGCGTGCCCG
TGTACAACAGCCCCGCCACTTCCTGGCCGAGACCTTCCTGCTGCTGCCCCAGGTGA
GCCCCTGGACAGCGGCCACCTGGGGCTGCGTGCTGACCTACCGCGACGGCTTCAAC
GTGAGCATCACCTACAACCTGAAGGTGCTGGGCCTGGAGCCCGTGGCCCCCCTGAC
CGTGTACGCCGCCGAGGGCAGCCGCGTGGAGCTGCCCTGCCACCTGCCCCCCGGCG
TGGGCACCCCCAGCCTGCTGATCGCCAAGTGGACCCCCCCGGCGGCGGCCCCGAG
CTGCCCGTGGCCGGCAAGAGCGGCAACTTCACCCTGCACCTGGAGGCCGTGGGCCT
GGCCCAGGCCGGCACCTACACCTGCAGCATCCACCTGCAGGGCCAGCAGCTGAACG
CCACCGTGACCCTGGCCGTGATCACCGTGACCCCCAAGAGCTTCGGCCTGCCCGGCA
GCCGCGGCAAGCTGCTGTGCGAGGTGACCCCCGCCAGCGGCAAGGAGCGCTTCGTG
TGGCGCCCCCTGAACAACCTGAGCCGCAGCTGCCCCGGCCCCGTGCTGGAGATCCA
GGAGGCCCGCCTGCTGGCCGAGCGCTGGCAGTGCCAGCTGTACGAGGGCCAGCGCC
TGCTGGGCGCCACCGTGTACGCCGCCGAGAGCAGCAGCGGCGCCCACAGCGCCCGC
CGCATCAGCGGCGACCTGAAGGGCGGCCACCTGGTGCTGGTGCTGATCCTGGGCGC
CCTGAGCCTGTTCCTGCTGGTGGCCGGCGCCTTCGGCTTCCACTGGTGGCGCAAGCA
GCTGCTGCTGCGCCGCTTCAGCGCCCTGGAGCACGGCATCCAGCCCTTCCCCGCCCA
GCGCAAGATCGAGGAGCTGGAGCGCGAGCTGGAGACCGAGATGGGCCAGGAGCCC
GAGCCCGAGCCCGAGCCCCAGCTGGAGCCCGAGCCCGCCAGCTGTAA (SEQ ID NO: 39)

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated monoclonal antibody, or an antigen-binding portion thereof, binding to LAG3, comprising a heavy chain variable region comprising a $V_H$ CDR1 region, a $V_H$ CDR2 region and a $V_H$ CDR3 region, and a light chain variable region comprising a $V_L$ CDR1 region, a $V_L$ CDR2 region and a $V_L$ CDR3 region, wherein the $V_H$ CDR1 region, the $V_H$ CDR2 region, the $V_H$ CDR3 region, the $V_L$ CDR1 region, the $V_L$ CDR2 region and the $V_L$ CDR3 region comprise the amino acid sequences set forth in (1) SEQ ID NOs: 1, 2, 3, 5, 6 and 7, respectively; (2) SEQ ID NOs: 1, 2, 4, 5, 6 and 8, respectively; or (3) SEQ ID NOs: 21, 22, 23, 24, 25 and 26, respectively.

2. The antibody, or the antigen-binding portion thereof, according to claim 1, wherein the heavy chain variable region comprises the amino acid sequence set forth in SEQ ID NOs: 9, 10, 11, 12, 13, 14, 27, 28, 29 or 30.

3. The antibody, or the antigen-binding portion thereof, according to claim 1, wherein the light chain variable region comprises the amino acid sequence set forth in SEQ ID NOs: 15, 16, 17, 18, 19, 20, 31, 32, 33 or 34.

4. The antibody, or the antigen-binding portion thereof, according to claim 2, wherein the heavy chain variable region and the light chain variable region comprise the amino acid sequences set forth in (1) SEQ ID NOs: 9 and 15, respectively; (2) SEQ ID NOs: 10 and 16, respectively; (3) SEQ ID NOs: 11 and 17, respectively; (4) SEQ ID NOs: 11 and 19, respectively; (5) SEQ ID NOs: 12 and 17, respectively; (6) SEQ ID NOs: 12 and 19, respectively; (7) SEQ ID NOs: 13 and 18, respectively; (8) SEQ ID NOs: 13 and 20, respectively; (9) SEQ ID NOs: 14 and 20, respectively; (10) SEQ ID NOs: 27 and 31, respectively; (11) SEQ ID NOs: 28 and 32, respectively; (12) SEQ ID NOs: 29 and 33, respectively; (13) SEQ ID NOs: 29 and 34, respectively; (14) SEQ ID NOs: 30 and 33, respectively; or (15) SEQ ID NOs: 30 and 34, respectively.

5. The antibody, or the antigen-binding portion thereof, according to claim 1, comprising a heavy chain constant region which is human IgG1 or IgG4 heavy chain constant region, linked to the heavy chain variable region, and/or a light chain constant region which is human kappa light chain constant region, linked to the light chain variable region.

6. The antibody, or the antigen-binding portion thereof, according to claim 5, wherein the heavy chain constant region comprises the amino acid sequence set forth in SEQ ID NO: 35, and the light chain constant region comprises the amino acid sequence set forth in SEQ ID NO: 36.

7. The antibody, or the antigen-binding portion thereof, according to claim 1, which (a) binds human LAG3; (b) binds monkey LAG3; (c) does not bind mouse LAG3; (d) blocks LAG3-MHC II complex interaction; (e) induces T cell activation; and/or (f) provides in vivo anti-tumor effect.

8. The antibody, or the antigen-binding portion thereof, according to claim 1, which is a mouse, chimeric or humanized antibody.

9. A pharmaceutical composition comprising the antibody, or the antigen-binding portion thereof, according to claim 1, and a pharmaceutically acceptable carrier.

10. The pharmaceutical composition according to claim 9, further comprising an anti-tumor agent, an anti-infective agent, or an anti-inflammatory agent.

11. A method for enhancing an immune response in a subject, comprising administering to the subject a therapeutically effect amount of the pharmaceutical composition according to claim 9, wherein the enhanced immune response is T cell activation or T cell stimulation.

12. The method according to claim 11, wherein the subject is further administered with an anti-tumor agent, a cytokine and/or a costimulatory antibody.

13. The method according to claim 12, wherein the anti-tumor agent is anti-PD-1 antibody, an anti-PD-L1 antibody, an anti-STAT3 antibody, an anti-ROR1 antibody, an anti-TIM3 antibody, and/or an anti-CTLA-4 antibody.

14. The method according to claim 12, wherein the cytokine is IL-2 or IL-21.

15. The method according to claim 12, wherein the costimulatory antibody is an anti-CD137 or an anti-GITR antibody.

16. A method for treating a solid tumor in a subject in need thereof, comprising administering to the subject a therapeutically effect amount of the pharmaceutical composition according to claim 9, wherein the solid tumor is colon adenocarcinoma.

17. The method according to claim 16, wherein the subject is further administered with an anti-tumor agent, a cytokine, and/or a costimulatory antibody.

18. The method according to claim 17, wherein the anti-tumor agent is anti-PD-1 antibody, an anti-PD-L1 antibody, an anti-STAT3 antibody, an anti-ROR1 antibody, an anti-TIM3 antibody, and/or an anti-CTLA-4 antibody.

19. The method according to claim 17, wherein the cytokine is IL-2 or IL-21.

20. The method according to claim 17, wherein the costimulatory antibody is an anti-CD137 or an anti-GITR antibody.

* * * * *